(12) United States Patent
Yang et al.

(10) Patent No.: US 10,927,160 B2
(45) Date of Patent: Feb. 23, 2021

(54) ENGINEERED INVARIANT NATURAL KILLER T (iNKT) CELLS AND METHODS OF MAKING AND USING THEREOF

(71) Applicant: The Regents of the University of California, Oakland, CA (US)

(72) Inventors: Lili Yang, Los Angeles, CA (US); Drake J. Smith, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 249 days.

(21) Appl. No.: 15/320,037

(22) PCT Filed: Jul. 8, 2015

(86) PCT No.: PCT/US2015/039465
§ 371 (c)(1),
(2) Date: Dec. 19, 2016

(87) PCT Pub. No.: WO2016/007570
PCT Pub. Date: Jan. 14, 2016

(65) Prior Publication Data
US 2017/0283481 A1 Oct. 5, 2017

Related U.S. Application Data

(60) Provisional application No. 62/022,301, filed on Jul. 9, 2014, provisional application No. 62/099,711, filed on Jan. 5, 2015.

(51) Int. Cl.
| | |
|---|---|
| *C07K 14/725* | (2006.01) |
| *C12N 5/0783* | (2010.01) |
| *A61K 48/00* | (2006.01) |
| *C07K 14/705* | (2006.01) |
| *A61K 39/00* | (2006.01) |

(52) U.S. Cl.
CPC .......... *C07K 14/7051* (2013.01); *A61K 48/00* (2013.01); *C07K 14/70503* (2013.01); *C12N 5/0646* (2013.01); *A61K 2039/5154* (2013.01); *C12N 2506/11* (2013.01); *C12N 2510/00* (2013.01); *C12N 2740/13043* (2013.01); *C12N 2830/48* (2013.01)

(58) Field of Classification Search
CPC .................................................. C07K 14/7051
See application file for complete search history.

(56) References Cited

U.S. PATENT DOCUMENTS

| 2005/0238626 | A1* | 10/2005 | Yang .................. A61K 39/0011 424/93.21 |
| 2013/0295142 | A1 | 11/2013 | Taniguchi et al. |
| 2013/0344095 | A1 | 12/2013 | Wang et al. |

FOREIGN PATENT DOCUMENTS

| EP | 2336303 A1 | 6/2011 |
| WO | 2009009063 A1 | 1/2009 |
| WO | 2012074116 A1 | 6/2012 |

OTHER PUBLICATIONS

Inoue et al. (Current Biology, vol. 15, 1114-1118, Jun. 21, 2005) (Year: 2005).*
Thedrez et al. (Blood. 2007;110:251-258). (Year: 2007).*
Sun et al. (Journal of Interferon & Cytokine Research. 2012; 32(11): 505-516). (Year: 2012).*
Gilmore et al. (Experimental Hematology 28 (2000) 1297-1305). (Year: 2000).*
Xu et al. (Nature Communications. (2018) 9:3875, p. 1-15) (Year: 2018).*
Van Kaer et al. (Immunotherapy. Published online Dec. 21, 2010; 3(1): 59-75) (Year: 2010).*
Shissier et al. (Mol Immunol. Jan. 2019 ; 105: 116-130. doi:10. 1016/j.moliimn.2018.09.023) (Year: 2019).*
Extended European Search Report received in EP15819070 dated Dec. 12, 2017.
Bendelac, et al., "Increased Interleukin 4 and Immunoglobulin E Production in Transgenic Mice Overexpressing NK1 T cells", Oct. 1, 1996, pp. 1285-1293, vol. 184, Publisher: J. Exp. Med.
Bilic, et al., "Concise Review: Induced Pluripotent Stem Cells Versus Embryonic Stem Cells: Close Enough or Yet Too Far Apart?", Dec. 23, 2011, p. 3341, vol. 30, Publisher: Stem Cells.
Medvedev, et al., "Induced Pluripotent Stem Cells: Problems and Advantages when Applying them in Regenerative Medicine", Oct. 4, 2010, vol. 2, No. 2(5), Publisher: Acta Naturae.
Panopoulos, et al., "Induced pluripotent stem cells in clinical hematology: potentials, progress, and remaining obstacles", , pp. 1-5, vol. 19, No. 00, Publisher: Curr Opin Hematol.
Ren, et al., "Generation of induced pluripotent stem cell-derived mice by reprogramming of a mature NKT cell", May 22, 2014, pp. 551-561, vol. 26, No. 10, Publisher: International Immunology.
Sun, et al., "Invariant natural killer T cells generated from human adult hematopoietic stem-progenitor cells are poly-functional", Jan. 5, 2015, pp. 48-57, vol. 72, Publisher: Cytokine.
Taniguchi, et al., "Essential requirement of an invariant V(alpha)14 T cell antigen receptor expression in the development of natural killer T cells", Oct. 1, 1996, pp. 11025-11028, vol. 93, Publisher: Proc. Natl. Acad. Sci. USA.
Vivier, et al., "Targeting natural killer cells and natural killer T cells in cancer", Apr. 1, 2012, pp. 239-252, vol. 12, Publisher: Nature Reviews Immunology.
Brennan, et al., "Invariant natural killer T cells: an innate activation scheme linked to diverse effector functions", Jan. 21, 2013, pp. 101-117, vol. 13, No. 2, Publisher: Nat. Rev. Immunol.

(Continued)

*Primary Examiner* — Scott Long
(74) *Attorney, Agent, or Firm* — Gates & Cooper LLP

(57) ABSTRACT

Disclosed are invariant natural killer T (iNKT) cells engineered using hematopoietic stem and progenitor cells (HSPCs) and methods of making and using thereof. Specifically, the engineered cells iNKT are genetically modified to contain at least one exogenous invariant natural killer T cell receptor (iNKT TCR) nucleic acid molecule. Further disclosed are iNKT TCR nucleotide sequences and codon optimized sequences for expression.

19 Claims, 13 Drawing Sheets

Specification includes a Sequence Listing.

(56) References Cited

OTHER PUBLICATIONS

IMGT_ DQ341448, "*Homo sapiens* clone J3N.5 T cell receptor alpha chain mRNA, complete cds, Accession No. DQ34144, Version 10", May 22, 2013.

"International Search Report received in PCT/US2015/039465", dated Dec. 14, 2015.

Lantz, et al., "An invariant T cell receptor alpha chain is used by a unique subset of major histocompatibility complex class I-specific CD4+ and CD4-8-T cells . . . ", Sep. 1, 1994, pp. 1097-1106, vol. 180, No. 3, Publisher: J. Exp. Med.

Matulis, et al., "Innate-Like Control of Human iNKT Cell Autoreactivity via the Hypervariable CDR3b Loop", Jun. 22, 2010, p. e100040, vol. 8, No. 6, Publisher: PLoS Biol.

Pilones, et al., "Invariant NKT Cells as Novel Targets for Immunotherapy in Solid Tumors", Sep. 2, 2012, pp. 1-11, vol. 2012, No. 720803, Publisher: Clin. Dev. Immunol.

"Written Opinion received in PCT/US2015/039465", dated Dec. 14, 2015.

Office Action Issued in Corresponding European Patent Application No. EP 15819070.2, dated Nov. 11, 2019.

Vatakis, et al., "Antitumor Activity From Antigen-Specific CD8 T Cells Generated In Vivo From Genetically Engineered Human Hematopoietic Stem Cells," PNAS, 108(51): e1408-e1416, 2011.

\* cited by examiner

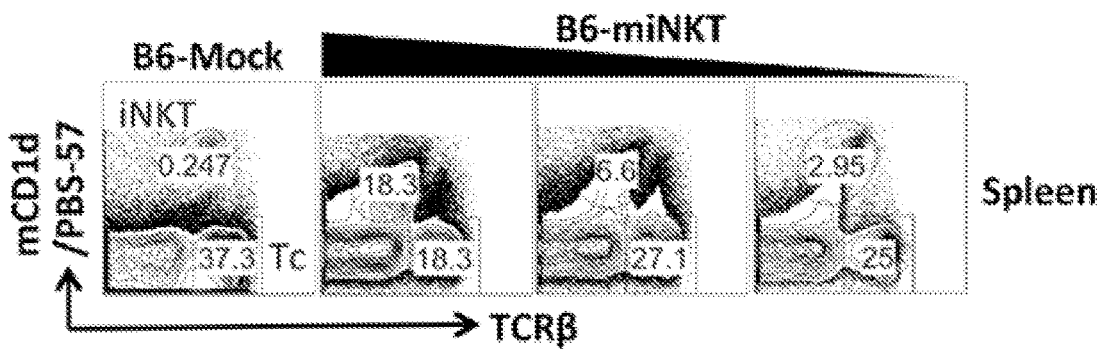
Figure 2D
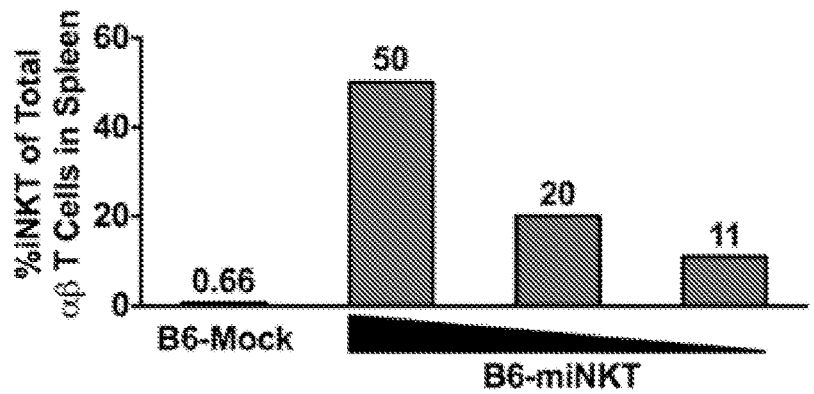
Figure 2E
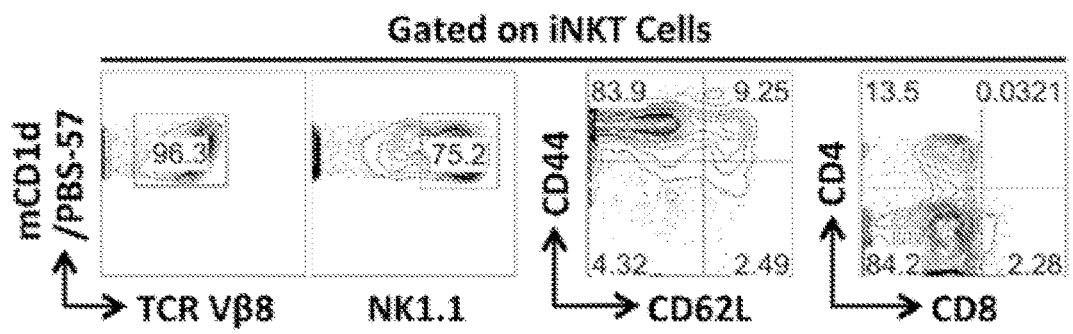
Figure 2F
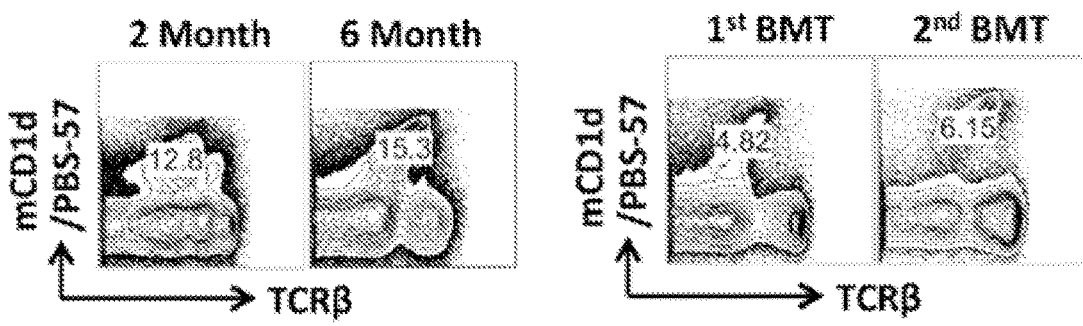
Figure 2G
Figure 2H

SEQUENCE LISTING

<160> NUMBER OF SEQ ID NOS: 65

<210> SEQ ID NO 1
<211> LENGTH: 75
<212> TYPE: DNA
<213> ORGANISM: Artificial Sequence
<220> FEATURE:
<223> OTHER INFORMATION: iNKT TCR-alpha chain cloned sequence

<400> SEQUENCE: 1
gtgggcgata gaggttcagc cttagggagg ctgcattttg gagctgggac tcagctgatt    60
gtcatacctg acatc    75

<210> SEQ ID NO 2
<211> LENGTH: 75
<212> TYPE: DNA
<213> ORGANISM: Artificial Sequence
<220> FEATURE:
<223> OTHER INFORMATION: iNKT TCR-beta chain cloned sequence

<400> SEQUENCE: 2
gccagcggtg atgctcgggg gggggaaat accctctatt ttggaaaagg aagccggctc    60
attgttgtag aggat    75

<210> SEQ ID NO 3
<211> LENGTH: 75
<212> TYPE: DNA
<213> ORGANISM: Artificial Sequence
<220> FEATURE:
<223> OTHER INFORMATION: iNKT TCR-beta chain cloned sequence

<400> SEQUENCE: 3
gccagcgggg ggacagtcca ttctggaaat acgctctatt ttggagaagg aagccggctc    60
attgttgtag aggat    75

<210> SEQ ID NO 4
<211> LENGTH: 75
<212> TYPE: DNA
<213> ORGANISM: Artificial Sequence
<220> FEATURE:
<223> OTHER INFORMATION: iNKT TCR-beta chain cloned sequence

<400> SEQUENCE: 4
gccagcggtg atacgggaca acaaacaca gaagtcttct ttggtaaagg aaccagactc    60
acagttgtag aggat    75

<210> SEQ ID NO 5
<211> LENGTH: 72
<212> TYPE: DNA
<213> ORGANISM: Artificial Sequence
<220> FEATURE:
<223> OTHER INFORMATION: iNKT TCR-beta chain cloned sequence

<400> SEQUENCE: 5
gccagcggtg aggggacagc aaacacagaa gtcttctttg gtaaaggaac cagactcaca    60
gttgtagagg at    72

<210> SEQ ID NO 6
<211> LENGTH: 69
<212> TYPE: DNA
<213> ORGANISM: Artificial Sequence
<220> FEATURE:
<223> OTHER INFORMATION: iNKT TCR-beta chain cloned sequence

```
<400> SEQUENCE: 6
gccagcggtg aggcagggaa cacagaagtc ttctttggta aaggaaccag actcacagtt      60
gtagaggat                                                              69

<210> SEQ ID NO 7
<211> LENGTH: 78
<212> TYPE: DNA
<213> ORGANISM: Artificial Sequence
<220> FEATURE:
<223> OTHER INFORMATION: iNKT TCR-alpha chain cloned sequence

<400> SEQUENCE: 7
gtgagcgaca gaggctcaac cctggggagg ctatactttg gaagaggaac tcagttgact      60
gtctggcctg atatccag                                                    78

<210> SEQ ID NO 8
<211> LENGTH: 75
<212> TYPE: DNA
<213> ORGANISM: Artificial Sequence
<220> FEATURE:
<223> OTHER INFORMATION: iNKT TCR-beta chain cloned sequence

<400> SEQUENCE: 8
agcagtgacc tccgaggaca gaacacagat acgcagtatt ttggcccagg cacccggctg      60
acagtgctcg aggac                                                       75

<210> SEQ ID NO 9
<211> LENGTH: 78
<212> TYPE: DNA
<213> ORGANISM: Artificial Sequence
<220> FEATURE:
<223> OTHER INFORMATION: iNKT TCR-beta chain cloned sequence

<400> SEQUENCE: 9
agcagtgaat taaaggaaac aggggttcaa gagacccagt acttcgggcc aggcacgcgg      60
ctcctggtgc tcgaggac                                                    78

<210> SEQ ID NO 10
<211> LENGTH: 69
<212> TYPE: DNA
<213> ORGANISM: Artificial Sequence
<220> FEATURE:
<223> OTHER INFORMATION: iNKT TCR-beta chain cloned sequence

<400> SEQUENCE: 10
agcagtgtat ctcagggcgg cactgaagct ttctttggac aaggcaccag actcacagtt      60
gtagaggac                                                              69

<210> SEQ ID NO 11
<211> LENGTH: 69
<212> TYPE: DNA
<213> ORGANISM: Artificial Sequence
<220> FEATURE:
<223> OTHER INFORMATION: iNKT TCR-beta chain cloned sequence

<400> SEQUENCE: 11
agcagtgtat ctcagggcgg cactgaagct ttctttggac aaggcaccag actcacagtt      60
gtagaggac                                                              69

<210> SEQ ID NO 12
```

```
<211> LENGTH: 72
<212> TYPE: DNA
<213> ORGANISM: Artificial Sequence
<220> FEATURE:
<223> OTHER INFORMATION: iNKT TCR-beta chain cloned sequence

<400> SEQUENCE: 12
agcagtgacc ggacaggcgt gaacactgaa gctttctttg acaaggcac cagactcaca        60 gttgtagagg ac                                                           72

<210> SEQ ID NO 13
<211> LENGTH: 72
<212> TYPE: DNA
<213> ORGANISM: Artificial Sequence
<220> FEATURE:
<223> OTHER INFORMATION: iNKT TCR-beta chain cloned sequence

<400> SEQUENCE: 13
agcagtgaac cggacagggg gggggctgaa gctttctttg acaaggcac cagactcaca        60 gttgtagagg ac                                                           72

<210> SEQ ID NO 14
<211> LENGTH: 32
<212> TYPE: DNA
<213> ORGANISM: Artificial Sequence
<220> FEATURE:
<223> OTHER INFORMATION: iNKT TCR-apha chain forward primer

<400> SEQUENCE: 14
gggagatact cagcaactct ggataaagat gc                                     32

<210> SEQ ID NO 15
<211> LENGTH: 27
<212> TYPE: DNA
<213> ORGANISM: Artificial Sequence
<220> FEATURE:
<223> OTHER INFORMATION: iNKT TCR-apha chain reverse primer

<400> SEQUENCE: 15
ccagattcca tggttttcgg cacattg                                           27

<210> SEQ ID NO 16
<211> LENGTH: 30
<212> TYPE: DNA
<213> ORGANISM: Artificial Sequence
<220> FEATURE:
<223> OTHER INFORMATION: iNKT TCR-beta chain forward primer

<400> SEQUENCE: 16
ggagatatcc ctgatggata caaggcctcc                                        30

<210> SEQ ID NO 17
<211> LENGTH: 30
<212> TYPE: DNA
<213> ORGANISM: Artificial Sequence
<220> FEATURE:
<223> OTHER INFORMATION: iNKT TCR-beta chain reverse primer

<400> SEQUENCE: 17
gggtagcctt ttgtttgttt gcaatctctg                                        30

<210> SEQ ID NO 18
<211> LENGTH: 831
<212> TYPE: DNA
<213> ORGANISM: Artificial Sequence
```

<220> FEATURE:
<223> OTHER INFORMATION: Human iNKT TCR-alpha chain cDNA

<400> SEQUENCE: 18

| | | |
|---|---|---|
| atgaaaaagc atctgacgac cttcttggtg attttgtggc tttatttttta tagggggaat | 60 |
| ggcaaaaacc aagtggagca gagtcctcag tccctgatca tcctggaggg aaagaactgc | 120 |
| actcttcaat gcaattatac agtgagcccc ttcagcaact taaggtggta taagcaagat | 180 |
| actgggagag gtcctgtttc cctgacaatc atgactttca gtgagaacac aaagtcgaac | 240 |
| ggaagatata cagcaactct ggatgcagac acaaagcaaa gctctctgca catcacagcc | 300 |
| tcccagctca gcgattcagc ctcctacatc tgtgtggtga gcgacagagg ctcaaccctg | 360 |
| gggaggctat actttggaag aggaactcag ttgactgtct ggcctgatat ccagaaccct | 420 |
| gaccctgccg tgtaccagct gagagactct aaatccagtg acaagtctgt ctgcctattc | 480 |
| accgattttg attctcaaac aaatgtgtca caaagtaagg attctgatgt gtatatcaca | 540 |
| gacaaaactg tgctagacat gaggtctatg gacttcaaga gcaacagtgc tgtggcctgg | 600 |
| agcaacaaat ctgactttgc atgtgcaaac gccttcaaca acagcattat tccagaagac | 660 |
| accttcttcc ccagcccaga aagttcctgt gatgtcaagc tggtcgagaa aagctttgaa | 720 |
| acagatacga acctaaactt tcaaaacctg tcagtgattg ggttccgaat cctcctcctg | 780 |
| aaagtggccg ggtttaatct gctcatgacg ctgcggctgt ggtccagctg a | 831 |

<210> SEQ ID NO 19
<211> LENGTH: 831
<212> TYPE: DNA
<213> ORGANISM: Artificial Sequence
<220> FEATURE:
<223> OTHER INFORMATION: Human iNKT TCR-alpha chain cDNA codon-optimized

<400> SEQUENCE: 19

| | | |
|---|---|---|
| atgaaaaagc atctgacaac attcctggtc attctgtggc tgtacttcta ccgaggcaac | 60 |
| ggcaaaaatc aggtggagca gtccccacag tccctgatca ttctggaggg gaagaactgc | 120 |
| actctgcagt gtaattacac cgtgtctccc tttagtaacc tgcgctggta taaacaggac | 180 |
| accggacgag gacccgtgag cctgacaatc atgactttct cagagaacac aaagagcaat | 240 |
| ggacggtaca ccgctacact ggacgcagat accaaacaga gctccctgca catcacagca | 300 |
| tctcagctgt cagatagcgc ctcctacatt tgcgtggtct ctgaccgagg gagtaccctg | 360 |
| ggccgactgt attttggaag ggggacccag ctgacagtgt ggcccgacat ccagaaccca | 420 |
| gatcccgccg tctaccagct gcgcgacagc aagtctagtg ataaaagcgt gtgcctgttc | 480 |
| acagactttg attctcagac taatgtctct cagagtaagg acagtgacgt gtacattact | 540 |
| gacaaaaccg tcctggatat gaggagcatg gacttcaagt caaacagcgc cgtggcttgg | 600 |
| tcaaacaaga gcgacttcgc atgcgccaat gcttttaaca attcaatcat tccagaggat | 660 |
| accttctttc ctagcccaga atcaagctgt gacgtgaagc tggtcgagaa agtttcgaa | 720 |
| actgatacca acctgaattt tcagaacctg tctgtgatcg gcttcagaat cctgctgctg | 780 |
| aaggtcgccg gctttaatct gctgatgaca ctgagactgt ggtcctcttg a | 831 |

<210> SEQ ID NO 20
<211> LENGTH: 276
<212> TYPE: PRT
<213> ORGANISM: Artificial Sequence
<220> FEATURE:
<223> OTHER INFORMATION: Human iNKT TCR-alpha chain

<400> SEQUENCE: 20

```
Met Lys Lys His Leu Thr Thr Phe Leu Val Ile Leu Trp Leu Tyr Phe
1               5                   10                  15
Tyr Arg Gly Asn Gly Lys Asn Gln Val Glu Gln Ser Pro Gln Ser Leu
            20                  25                  30
Ile Ile Leu Glu Gly Lys Asn Cys Thr Leu Gln Cys Asn Tyr Thr Val
        35                  40                  45
Ser Pro Phe Ser Asn Leu Arg Trp Tyr Lys Gln Asp Thr Gly Arg Gly
    50                  55                  60
Pro Val Ser Leu Thr Ile Met Thr Phe Ser Glu Asn Thr Lys Ser Asn
65                  70                  75                  80
Gly Arg Tyr Thr Ala Thr Leu Asp Ala Asp Thr Lys Gln Ser Ser Leu
                85                  90                  95
His Ile Thr Ala Ser Gln Leu Ser Asp Ser Ala Ser Tyr Ile Cys Val
            100                 105                 110
Val Ser Asp Arg Gly Ser Thr Leu Gly Arg Leu Tyr Phe Gly Arg Gly
        115                 120                 125
Thr Gln Leu Thr Val Trp Pro Asp Ile Gln Asn Pro Asp Pro Ala Val
    130                 135                 140
Tyr Gln Leu Arg Asp Ser Lys Ser Ser Asp Lys Ser Val Cys Leu Phe
145                 150                 155                 160
Thr Asp Phe Asp Ser Gln Thr Asn Val Ser Gln Ser Lys Asp Ser Asp
                165                 170                 175
Val Tyr Ile Thr Asp Lys Thr Val Leu Asp Met Arg Ser Met Asp Phe
            180                 185                 190
Lys Ser Asn Ser Ala Val Ala Trp Ser Asn Lys Ser Asp Phe Ala Cys
        195                 200                 205
Ala Asn Ala Phe Asn Asn Ser Ile Ile Pro Glu Asp Thr Phe Phe Pro
    210                 215                 220
Ser Pro Glu Ser Ser Cys Asp Val Lys Leu Val Glu Lys Ser Phe Glu
225                 230                 235                 240
Thr Asp Thr Asn Leu Asn Phe Gln Asn Leu Ser Val Ile Gly Phe Arg
                245                 250                 255
Ile Leu Leu Leu Lys Val Ala Gly Phe Asn Leu Leu Met Thr Leu Arg
            260                 265                 270
Leu Trp Ser Ser
        275
```

<210> SEQ ID NO 21
<211> LENGTH: 336
<212> TYPE: DNA
<213> ORGANISM: Artificial Sequence
<220> FEATURE:
<223> OTHER INFORMATION: Human iNKT TCR-beta chain cDNA (before D/J/N region)

<400> SEQUENCE: 21

```
atgactatca ggctcctctg ctacatgggc ttttattttc tggggcagg cctcatggaa      60
gctgacatct accagacccc aagataccett gttataggga caggaaagaa gatcactctg     120
gaatgttctc aaaccatggg ccatgacaaa atgtactggt atcaacaaga tccaggaatg     180
gaactacacc tcatccacta ttcctatgga gttaattcca cagagaaggg agatcttttcc    240
tctgagtcaa cagtctccag aataaggacg gagcattttc ccctgacccct ggagtctgcc   300
aggccctcac atacctctca gtacctctgt gccagc                               336
```

<210> SEQ ID NO 22
<211> LENGTH: 336
<212> TYPE: DNA
<213> ORGANISM: Artificial Sequence
<220> FEATURE:
<223> OTHER INFORMATION: Human iNKT TCR-beta chain cDNA codon-optimized

<400> SEQUENCE: 22

```
atgaccatcc ggctgctgtg ctacatgggc ttctattttc tgggggcagg cctgatggaa    60
gccgacatct accagactcc agatacctg gtcatcggaa ccgggaagaa aattacactg     120
gagtgttccc agacaatggg ccacgataag atgtactggt atcagcagga ccctgggatg    180
gaactgcacc tgatccatta ctcctatggc gtgaactcta ccgagaaggg cgacctgagc    240
agcgaatcca ccgtctctcg aattaggaca gagcactttc ctctgactct ggaaagcgcc    300
cgaccaagtc atacatcaca gtacctgtgc gctagc                              336
```

<210> SEQ ID NO 23
<211> LENGTH: 112
<212> TYPE: PRT
<213> ORGANISM: Artificial Sequence
<220> FEATURE:
<223> OTHER INFORMATION: Human iNKT TCR-beta chain

<400> SEQUENCE: 23

```
Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110
```

<210> SEQ ID NO 24
<211> LENGTH: 60
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 24

```
gtagcggttg ggccccaaga gacccagtac ttcgggccag gcacgcggct cctggtgctc    60
```

<210> SEQ ID NO 25
<211> LENGTH: 60
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 25

```
gtggcagtcg gacctcagga gacccagtac ttcggacccg gcacccgcct gctggtgctg    60
```

```
<210> SEQ ID NO 26
<211> LENGTH: 20
<212> TYPE: PRT
<213> ORGANISM: Artificial Sequence
<220> FEATURE:
<223> OTHER INFORMATION: Human iNKT TCR Beta Chain Diverse Region
      (D/J/N)

<400> SEQUENCE: 26

Val Ala Val Gly Pro Gln Glu Thr Gln Tyr Phe Gly Pro Gly Thr Arg
1               5                   10                  15

Leu Leu Val Leu
            20

<210> SEQ ID NO 27
<211> LENGTH: 54
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 27
agtgggccag ggtacgagca gtacttcggg ccgggcacca ggctcacggt caca          54

<210> SEQ ID NO 28
<211> LENGTH: 54
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 28
tcaggacccg gctacgagca gtatttcggc cccggaactc ggctgaccgt gacc          54

<210> SEQ ID NO 29
<211> LENGTH: 18
<212> TYPE: PRT
<213> ORGANISM: Artificial Sequence
<220> FEATURE:
<223> OTHER INFORMATION: Human iNKT TCR Beta Chain Diverse Region
      (D/J/N)

<400> SEQUENCE: 29

Ser Gly Pro Gly Tyr Glu Gln Tyr Phe Gly Pro Gly Thr Arg Leu Thr
1               5                   10                  15

Val Thr

<210> SEQ ID NO 30
<211> LENGTH: 57
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 30 agtcccccaat taaacactga agctttcttt ggacaaggca ccagactcac agttgta       57

<210> SEQ ID NO 31
<211> LENGTH: 57
<212> TYPE: DNA
<213> ORGANISM: Artificial Sequence
<220> FEATURE:
<223> OTHER INFORMATION: Human iNKT TCR Beta Chain Diverse Region
```

```
                                (D/J/N)

<400> SEQUENCE: 31
tctccacagc tgaacaccga ggccttcttc gggcagggca caaggcttac cgtggtg       57

<210> SEQ ID NO 32
<211> LENGTH: 19
<212> TYPE: PRT
<213> ORGANISM: Artificial Sequence
<220> FEATURE:
<223> OTHER INFORMATION: Human iNKT TCR Beta Chain Diverse Region
      (D/J/N)

<400> SEQUENCE: 32

Ser Pro Gln Leu Asn Thr Glu Ala Phe Phe Gly Gln Gly Thr Arg Leu
1               5                   10                  15

Thr Val Val

<210> SEQ ID NO 33
<211> LENGTH: 78
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 33
agtgaattgc gggcgctcgg gcccagctcc tataattcac ccctccactt tgggaacggg    60
accaggctca ctgtgaca                                                  78

<210> SEQ ID NO 34
<211> LENGTH: 78
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 34
tccgaactcc gagccctggg gcctagctcc tacaatagcc ccctgcactt tggcaacgga    60
accaggctga cggtcacc                                                  78

<210> SEQ ID NO 35
<211> LENGTH: 26
<212> TYPE: PRT
<213> ORGANISM: Artificial Sequence
<220> FEATURE:
<223> OTHER INFORMATION: Human iNKT TCR Beta Chain Diverse Region
      (D/J/N)

<400> SEQUENCE: 35

Ser Glu Leu Arg Ala Leu Gly Pro Ser Ser Tyr Asn Ser Pro Leu His
1               5                   10                  15

Phe Gly Asn Gly Thr Arg Leu Thr Val Thr
                20                  25

<210> SEQ ID NO 36
<211> LENGTH: 60
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 36
```
agtgaacagg ggactactgc gggagctttc tttggacaag gcaccagact cacagttgta    60

```
<210> SEQ ID NO 37
<211> LENGTH: 60
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 37
```
tccgaacagg gaaccacagc aggagccttc ttcggtcagg gaacaagact gacagtcgtg    60

```
<210> SEQ ID NO 38
<211> LENGTH: 20
<212> TYPE: PRT
<213> ORGANISM: Artificial Sequence
<220> FEATURE:
<223> OTHER INFORMATION: Human iNKT TCR Beta Chain Diverse Region
      (D/J/N)

<400> SEQUENCE: 38
```

Ser Glu Gln Gly Thr Thr Ala Gly Ala Phe Phe Gly Gln Gly Thr Arg
1               5                   10                  15

Leu Thr Val Val
            20

```
<210> SEQ ID NO 39
<211> LENGTH: 66
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 39
```
agtgagtcac gacatgcgac aggaaacacc atatattttg agagggaag ttggctcact    60 gttgta                                                             66

```
<210> SEQ ID NO 40
<211> LENGTH: 66
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 40
```
agcgagagca ggcacgcaac cgggaacacc atatactttg gcgagggctc ctggctgact    60
gtggtg                                                             66

```
<210> SEQ ID NO 41
<211> LENGTH: 22
<212> TYPE: PRT
<213> ORGANISM: Artificial Sequence
<220> FEATURE:
<223> OTHER INFORMATION: Human iNKT TCR Beta Chain Diverse Region
      (D/J/N)

<400> SEQUENCE: 41
```

Ser Glu Ser Arg His Ala Thr Gly Asn Thr Ile Tyr Phe Gly Glu Gly
1               5                   10                  15

Ser Trp Leu Thr Val Val
            20

<210> SEQ ID NO 42
<211> LENGTH: 69
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 42
agtgtacccg ggaacgacag gggcaatgaa aaactgtttt ttggcagtgg aacccagctc    60
tctgtcttg                                                            69

<210> SEQ ID NO 43
<211> LENGTH: 69
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 43
tccgtgcctg gcaacgatag aggtaacgag aagctgtttt tcggatccgg cacacagctg    60
tctgtcctg                                                            69

<210> SEQ ID NO 44
<211> LENGTH: 23
<212> TYPE: PRT
<213> ORGANISM: Artificial Sequence
<220> FEATURE:
<223> OTHER INFORMATION: Human iNKT TCR Beta Chain Diverse Region
      (D/J/N)

<400> SEQUENCE: 44

Ser Val Pro Gly Asn Asp Arg Gly Asn Glu Lys Leu Phe Phe Gly Ser
1               5                   10                  15

Gly Thr Gln Leu Ser Val Leu
            20

<210> SEQ ID NO 45
<211> LENGTH: 72
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 45
agtgaagggg ggggccttaa gctagccaaa aacattcagt acttcggcgc cgggacccgg    60
ctctcagtgc tg                                                        72

<210> SEQ ID NO 46
<211> LENGTH: 72
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 46
agtgagggag ggggactgaa gctggctaag aatattcagt acttcggcgc cggcactaga    60
ctgtctgtgc tg                                                        72

<210> SEQ ID NO 47
<211> LENGTH: 24
<212> TYPE: PRT
<213> ORGANISM: Artificial Sequence
<220> FEATURE:
<223> OTHER INFORMATION: Human iNKT TCR Beta Chain Diverse Region
      (D/J/N)

<400> SEQUENCE: 47

Ser Glu Gly Gly Gly Leu Lys Leu Ala Lys Asn Ile Gln Tyr Phe Gly
1               5                   10                  15

Ala Gly Thr Arg Leu Ser Val Leu
            20

<210> SEQ ID NO 48
<211> LENGTH: 69
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 48
agtgaattcg cctcttcggt acgtggaaac accatatatt ttggagaggg aagttggctc    60
actgttgta                                                            69

<210> SEQ ID NO 49
<211> LENGTH: 69
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 49
tctgagttcg cgagcagcgt ccggggtaat accatttact cgggaagg cagctggctg      60 accgtggtg                                                            69

<210> SEQ ID NO 50
<211> LENGTH: 23
<212> TYPE: PRT
<213> ORGANISM: Artificial Sequence
<220> FEATURE:
<223> OTHER INFORMATION: Human iNKT TCR Beta Chain Diverse Region
      (D/J/N)

<400> SEQUENCE: 50

Ser Glu Phe Ala Ser Ser Val Arg Gly Asn Thr Ile Tyr Phe Gly Glu
1               5                   10                  15

Gly Ser Trp Leu Thr Val Val
            20

<210> SEQ ID NO 51
<211> LENGTH: 60
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 51
agtgcggcat taggccggga gacccagtac ttcgggccag gcacgcggct cctggtgctc    60

<210> SEQ ID NO 52
<211> LENGTH: 60

```
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 52
tctgcagccc ttggccgaga gactcagtac ttcggccctg gcacaagact gctcgtgctc    60

<210> SEQ ID NO 53
<211> LENGTH: 20
<212> TYPE: PRT
<213> ORGANISM: Artificial Sequence
<220> FEATURE:
<223> OTHER INFORMATION: Human iNKT TCR Beta Chain Diverse Region
      (D/J/N)

<400> SEQUENCE: 53

Ser Ala Ala Leu Gly Arg Glu Thr Gln Tyr Phe Gly Pro Gly Thr Arg
1               5                  10                  15
Leu Leu Val Leu
            20

<210> SEQ ID NO 54
<211> LENGTH: 63
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 54
agtgcctccg ggggtgaatc ctacgagcag tacttcgggc cgggcaccag gctcacggtc    60
aca                                                                 63

<210> SEQ ID NO 55
<211> LENGTH: 63
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 55
agcgcctccg gaggagagtc atacgaacag tatttcggcc ctggcacacg cctcactgtg    60
acc                                                                 63

<210> SEQ ID NO 56
<211> LENGTH: 21
<212> TYPE: PRT
<213> ORGANISM: Artificial Sequence
<220> FEATURE:
<223> OTHER INFORMATION: Human iNKT TCR Beta Chain Diverse Region
      (D/J/N)

<400> SEQUENCE: 56

Ser Ala Ser Gly Gly Glu Ser Tyr Glu Gln Tyr Phe Gly Pro Gly Thr
1               5                  10                  15
Arg Leu Thr Val Thr
            20

<210> SEQ ID NO 57
<211> LENGTH: 90
<212> TYPE: DNA
<213> ORGANISM: Artificial Sequence
```

```
<220> FEATURE:
<223> OTHER INFORMATION: Human iNKT TCR Beta Chain Diverse Region
      (D/J/N)

<400> SEQUENCE: 57
agcggtcggg tctcgggggg cgattccctc atagcgtttc taggccaaga gacccagtac    60
ttcgggccag gcacgcggct cctggtgctc                                     90

<210> SEQ ID NO 58
<211> LENGTH: 90
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 58
tcaggacgag tgtccggagg ggatagcctc atcgcatttc tggggcagga aactcagtac    60
ttcggacccg gaacacgcct cctggtgctg                                     90

<210> SEQ ID NO 59
<211> LENGTH: 30
<212> TYPE: PRT
<213> ORGANISM: Artificial Sequence
<220> FEATURE:
<223> OTHER INFORMATION: Human iNKT TCR Beta Chain Diverse Region
      (D/J/N)

<400> SEQUENCE: 59

Ser Gly Arg Val Ser Gly Gly Asp Ser Leu Ile Ala Phe Leu Gly Gln
1               5                   10                  15

Glu Thr Gln Tyr Phe Gly Pro Gly Thr Arg Leu Leu Val Leu
            20                  25                  30

<210> SEQ ID NO 60
<211> LENGTH: 69
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 60
agtgtacccg ggaacgacag gggcaatgaa aaactgtttt ttggcagtgg aacccagctc    60
tctgtcttg                                                            69

<210> SEQ ID NO 61
<211> LENGTH: 69
<212> TYPE: DNA
<213> ORGANISM: Artificial Sequence
<220> FEATURE:
<223> OTHER INFORMATION: Human iNKT TCR Beta Chain Diverse Region
      (D/J/N)

<400> SEQUENCE: 61
tccgtgcctg gcaacgatag aggtaacgag aagctgtttt tcggatccgg cacacagctg    60
tctgtcctg                                                            69

<210> SEQ ID NO 62
<211> LENGTH: 23
<212> TYPE: PRT
<213> ORGANISM: Artificial Sequence
<220> FEATURE:
<223> OTHER INFORMATION: Human iNKT TCR Beta Chain Diverse Region
```

(D/J/N)

<400> SEQUENCE: 62

Ser Val Pro Gly Asn Asp Arg Gly Asn Glu Lys Leu Phe Phe Gly Ser
1               5                   10                  15

Gly Thr Gln Leu Ser Val Leu
            20

<210> SEQ ID NO 63
<211> LENGTH: 534
<212> TYPE: DNA
<213> ORGANISM: Artificial Sequence
<220> FEATURE:
<223> OTHER INFORMATION: Human iNKT TCR-beta chain cDNA (after D/J/N
      region)

<400> SEQUENCE: 63
gaggacctga acaaggtgtt cccacccgag gtcgctgtgt ttgagccatc agaagcagag      60
atctcccaca cccaaaaggc cacactggtg tgcctggcca caggcttctt ccctgaccac     120
gtggagctga gctggtgggt gaatgggaag gaggtgcaca gtggggtcag cacggacccg     180
cagcccctca aggagcagcc cgccctcaat gactccagat actgcctgag cagccgcctg     240
agggtctcgg ccaccttctg gcagaacccc cgcaaccact tccgctgcca agtccagttc     300
tacgggctct cggagaatga cgagtggacc caggataggg ccaaaccecgt cacccagatc     360 gtcagcgccg aggcctgggg tagagcagac tgtggcttta cctcggtgtc ctaccagcaa     420
ggggtcctgt ctgccaccat cctctatgag atcctgctag gaaggccac cctgtatgct      480 gtgctggtca gcgcccttgt gttgatggcc atggtcaaga gaaaggattt ctga           534

<210> SEQ ID NO 64
<211> LENGTH: 534
<212> TYPE: DNA
<213> ORGANISM: Artificial Sequence
<220> FEATURE:
<223> OTHER INFORMATION: Human iNKT TCR-beta chain cDNA codon-optimized
      (after D/J/N region)

<400> SEQUENCE: 64
gaggacctga ataaggtgtt cccccctgag gtggctgtct ttgaaccaag tgaggcagaa      60
atttcacata cacagaaagc caccctggtg tgcctggcta ccggcttctt tcccgatcac     120
gtggagctga gctggtgggt caacggcaag gaagtgcata gcggagtctc cacagaccca     180
cagcccctga agagcagcc tgctctgaat gattccagat actgcctgtc tagtagactg      240
cgggtgtctg ccaccttctg gcagaaccca aggaatcatt tcagatgtca ggtgcagttt     300
tatggcctga gcgagaacga tgaatggact caggacaggg ctaagccagt gacccagatc     360
gtcagcgcag aggcctgggg aagagcagac tgcgggttta caagcgtgag ctatcagcag     420
ggcgtcctga gcgccacaat cctgtacgaa attctgctgg aaaggccac tctgtatgct      480 gtgctggtct ccgctctggt gctgatggca atggtcaagc ggaaagattt ctga            534

<210> SEQ ID NO 65
<211> LENGTH: 177
<212> TYPE: PRT
<213> ORGANISM: Artificial Sequence
<220> FEATURE:
<223> OTHER INFORMATION: Human iNKT TCR-beta chain (after D/J/N region)

<400> SEQUENCE: 65

Glu Asp Leu Asn Lys Val Phe Pro Pro Glu Val Ala Val Phe Glu Pro

-continued

```
1               5                   10                  15
Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
            50                  55                  60

Glu Gln Pro Ala Leu Asn Asp Ser Arg Tyr Cys Leu Ser Ser Arg Leu
65                      70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
            130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe
```

ENGINEERED INVARIANT NATURAL KILLER T (iNKT) CELLS AND METHODS OF MAKING AND USING THEREOF

CROSS-REFERENCE TO RELATED APPLICATIONS

This application claims the benefit of U.S. Application No. 62/022,301, filed Jul. 9, 2014, and U.S. Application No. 62/099,711, filed Jan. 5, 2015, both of which are herein incorporated by reference in their entirety.

ACKNOWLEDGEMENT OF GOVERNMENT SUPPORT

This invention was made with Government support under DP2 CA196335 and P50 CA092131, awarded by the National Institutes of Health. The Government has certain rights in the invention.

REFERENCE TO A SEQUENCE LISTING SUBMITTED VIA EFS-WEB

The content of the ASCII text file of the sequence listing named "20170611_034044_149US1_subseq_ST25" which is 26.3 kb in size was created on Jun. 11, 2017, and electronically submitted via EFS-Web on Jun. 13, 2017, is incorporated herein by reference in its entirety.

BACKGROUND OF THE INVENTION

1. Field of the Invention

The present invention relates to invariant natural killer T (iNKT) cells engineered from hematopoietic stem and progenitor cells (HSPCs) and methods of making and using thereof.

2. Description of the Related Art

Invariant natural killer T (iNKT) cells are a small population of αβ T lymphocytes highly conserved from mice to humans. iNKT cells have been suggested to play important roles in regulating many diseases, including cancer, infections, allergies, and autoimmunity. When stimulated, iNKT cells rapidly release a large amount of effector cytokines like IFN-γ and IL-4, both as a cell population and at the single-cell level. These cytokines then activate various immune effector cells, such as natural killer (NK) cells and dendritic cells (DCs) of the innate immune system, as well as CD4 helper and CD8 cytotoxic conventional αβ T cells of the adaptive immune system via activated DCs. Because of their unique activation mechanism, iNKT cells can attack multiple diseases independent of antigen- and MHC-restrictions, making them attractive universal therapeutic agents. Notably, because of the capacity of effector NK cells and conventional αβ T cells to specifically recognize diseased tissue cells, iNKT cell-induced immune reactions result in limited off-target side effects.

In the past 2 decades, a series of iNKT cell-based clinical trials have been conducted, mainly targeting cancer. A recent trial reported encouraging antitumor immunity in patients with head and neck squamous cell carcinoma, attesting to the potential of iNKT cell-based immunotherapies. However, most clinical trials to date have yielded unsatisfactory results since they are based on the direct stimulation or ex vivo expansion of endogenous iNKT cells, thereby yielding only short-term, limited clinical benefits to a small number of patients. The low frequency and high variability of iNKT cells in humans (about 0.01-1% in blood), as well as the rapid depletion of these cells post-stimulation, are considered to be the major stumbling blocks limiting the success of these trials.

iNKT cells have been engineered from induced pluripotent stem (iPS) cells. See U.S. Pat. No. 8,945,922. iPS cells are produced by transducing a somatic cell with exogenous nuclear reprogramming factors, Oct4, Sox2, Klf4, and c-Myc, or the like. Unfortunately, since the transcription level of the exogenous nuclear reprogramming factors decreases with cell transition into the pluripotent state, the efficiency of stable iPS cell line production can decrease. Additionally, transcription of the exogenous nuclear reprogramming factors can resume in iPS cells and cause neoplastic development from cells derived from iPS cells since Oct4, Sox2, Klf4, and c-Myc are oncogenes that lead to oncogenesis. See Medvedev, et al. (2010) Acta Naturae 2(5):18-27.

Thus, a need exists for engineered iNKT cells that are not derived from iPS cells.

SUMMARY OF THE INVENTION

In some embodiments, the present invention provides an engineered cell which is a cell genetically modified to contain at least one exogenous invariant natural killer T cell receptor (iNKT TCR) nucleic acid molecule. In some embodiments, the cell is a hematopoietic stem cell. In some embodiments, the cell is a hematopoietic progenitor cell. In some embodiments, the cell is a human cell. In some embodiments, the cell is a CD34$^+$ cell. In some embodiments, the cell is a human CD34$^+$ cell. In some embodiments, the cell is a recombinant cell. In some embodiments, the cell is of a cultured strain. In some embodiments, the iNKT TCR nucleic acid molecule is from a human invariant natural killer T cell. In some embodiments, the iNKT TCR nucleic acid molecule comprises one or more nucleic acid sequences obtained from a human iNKT TCR. In some embodiments, the iNKT TCR nucleic acid sequence can be obtained from any subset of iNKT cells, such as the CD4/DN/CD8 subsets or the subsets that produce Th1, Th2, or Th17 cytokines, and includes double negative iNKT cells. In some embodiments, the iNKT TCR nucleic acid sequence is obtained from an iNKT cell from a donor who had or has a cancer such as melanoma, kidney cancer, lung cancer, prostate cancer, breast cancer, lymphoma, leukemia, a hematological malignancy, and the like. In some embodiments, the iNKT TCR nucleic acid molecule has a TCRα sequence from one iNKT cell and a TCRβ sequence from a different iNKT cell. In some embodiments, the iNKT cell from which the TCRα sequence is obtained and the iNKT cell from which the TCRβ sequence is obtained are from the same donor. In some embodiments, the donor of the iNKT cell from which the TCRα sequence is obtained is different from the donor of the iNKT cell from which the TCRβ sequence is obtained. In some embodiments, the TCRα sequence and/or the TCRβ sequence are codon optimized for expression. In some embodiments, the TCRα sequence and/or the TCRβ sequence are modified to encode a polypeptide having one or more amino acid substitutions, deletions, and/or truncations compared to the polypeptide encoded by the unmodified sequence. In some embodiments, the iNKT TCR nucleic acid molecule encodes a T cell receptor that recognizes α-galactosylceramide (α-GalCer) presented on CD1d. In some embodiments, the iNKT TCR nucleic acid molecule comprises one or more sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 18, SEQ ID NO: 19, SEQ ID NO: 21 and SEQ ID NO: 63, SEQ ID NO: 22 and SEQ ID NO: 64, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, SEQ ID NO: 52, SEQ ID NO: 54, SEQ ID NO: 55, SEQ ID NO: 57, SEQ ID NO: 58, SEQ ID NO: 60, and SEQ ID NO: 61. In some embodiments, the iNKT TCR nucleic acid molecule encodes a polypeptide comprising an amino acid sequence selected from the group consisting of: SEQ ID NO: 20, SEQ ID NO: 23 and SEQ ID NO: 65, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56, SEQ ID NO: 59, and SEQ ID NO: 62. In some embodiments, the engineered cell lacks exogenous oncogenes, such as Oct4, Sox2, Klf4, c-Myc, and the like. In some embodiments, the engineered cell is a functional iNKT cell. In some embodiments, the engineered cell is capable of producing one or more cytokines and/or chemokines such as IFNγ, TNFα, TGFβ, GM-CSF, IL-2, IL-4, IL-5, IL-6, IL-10, IL-13, IL-17, IL-21, RANTES, Eotaxin, MIP-1α, MIP-1β, and the like.

In some embodiments, the present invention provides a method obtaining an engineered cell of the present invention, which comprises transducing the cell with at least one exogenous invariant natural killer T cell receptor (iNKT TCR) nucleic acid molecule. In some embodiments, the cell is a hematopoietic stem cell. In some embodiments, the cell is a hematopoietic progenitor cell. In some embodiments, the cell is a human cell. In some embodiments, the cell is a CD34+ cell. In some embodiments, the cell is a human CD34+ cell. In some embodiments, the cell is a recombinant cell. In some embodiments, the cell is of a cultured strain. In some embodiments, the iNKT TCR nucleic acid molecule is from a human invariant natural killer T cell. In some embodiments, the iNKT TCR nucleic acid molecule comprises one or more nucleic acid sequences obtained from a human iNKT TCR. In some embodiments, the iNKT TCR nucleic acid sequence can be obtained from any subset of iNKT cells, such as the CD4/DN/CD8 subsets or the subsets that produce Th1, Th2, or Th17 cytokines, and includes double negative iNKT cells. In some embodiments, the iNKT TCR nucleic acid sequence is obtained from an iNKT cell from a donor who had or has a cancer such as melanoma, kidney cancer, lung cancer, prostate cancer, breast cancer, lymphoma, leukemia, a hematological malignancy, and the like. In some embodiments, the iNKT TCR nucleic acid molecule has a TCRα sequence from one iNKT cell and a TCRβ sequence from a different iNKT cell. In some embodiments, the iNKT cell from which the TCRα sequence is obtained and the iNKT cell from which the TCRβ sequence is obtained are from the same donor. In some embodiments, the donor of the iNKT cell from which the TCRα sequence is obtained is different from the donor of the iNKT cell from which the TCRβ sequence is obtained. In some embodiments, the TCRα sequence and/or the TCRβ sequence are codon optimized for expression. In some embodiments, the TCRα sequence and/or the TCRβ sequence are modified to encode a polypeptide having one or more amino acid substitutions, deletions, and/or truncations compared to the polypeptide encoded by the unmodified sequence. In some embodiments, the iNKT TCR nucleic acid molecule encodes a T cell receptor that recognizes α-galactosylceramide (α-GalCer) presented on CD1d. In some embodiments, the iNKT TCR nucleic acid molecule comprises one or more sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 18, SEQ ID NO: 19, SEQ ID NO: 21 and SEQ ID NO: 63, SEQ ID NO: 22 and SEQ ID NO: 64, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, SEQ ID NO: 52, SEQ ID NO: 54, SEQ ID NO: 55, SEQ ID NO: 57, SEQ ID NO: 58, SEQ ID NO: 60, and SEQ ID NO: 61. In some embodiments, the iNKT TCR nucleic acid molecule encodes a polypeptide comprising an amino acid sequence selected from the group consisting of: SEQ ID NO: 20, SEQ ID NO: 23 and SEQ ID NO: 65, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56, SEQ ID NO: 59, and SEQ ID NO: 62. In some embodiments, the engineered cell lacks exogenous oncogenes, such as Oct4, Sox2, Klf4, c-Myc, and the like. In some embodiments, the engineered cell is a functional iNKT cell. In some embodiments, the engineered cell is capable of producing one or more cytokines and/or chemokines such as IFNγ, TNFα, TGFβ, GM-CSF, IL-2, IL-4, IL-5, IL-6, IL-10, IL-13, IL-17, IL-21, RANTES, Eotaxin, MIP-1α, MIP-1β, and the like. In some embodiments, the method further comprises expanding the cell transduced with the iNKT TCR nucleic acid sequence in vitro. In some embodiments, the method further comprises engrafting the cell transduced with the iNKT TCR nucleic acid molecule in a subject to generate clonal populations of the engineered cell. In some embodiments, the subject contains human thymus tissue. In some embodiments, the subject is an animal such as a mouse. In some embodiments, the subject is human. In some embodiments, the method further comprises culturing the cell transduced with the iNKT TCR nucleic acid molecule with OP9-DL1 stromal cells and then culturing with CD1d-expressing artificial antigen-presenting cells. In some embodiments, the method further comprises culturing the cell transduced with the iNKT TCR nucleic acid molecule with MS5-DL4 stromal cells and then culturing with CD1d-expressing artificial antigen-presenting cells. In some embodiments, the method further comprises cloning the T cell receptor of an invariant natural killer T (iNKT) cell. In some embodiments, the iNKT cell is obtained from a donor. In some embodiments, the iNKT cell is obtained from a subject to be treated with the engineered cell. In some embodiments, the iNKT cell is obtained from an animal such as a mouse. In some embodiments, the iNKT cell is obtained from a human. In some embodiments, the iNKT TCR nucleic acid molecule is contained in an expression vector. In some embodiments, the expression vector is a lentiviral expression vector. In some embodiments, the expression vector is a MIG vector in which the iNKT TCR nucleic acid molecule replaces the IRES-EGFP segment of the MIG vector. In some embodiments, the expression vector is phiNKT-EGFP In some embodiments, the present invention provides a composition comprising one or more engineered cells of the present invention and/or one or more engineered cells made by a method according to the present invention. In some embodiments, the compositions comprise the one or more engineered cells at a concentration of about $1.0 \times 10^5$ to $1.0 \times 10^7$ cells/ml. In some embodiments, the composition further comprises a pharmaceutically acceptable carrier. In some embodiments, the composition further comprises a medium suitable for culturing the engineered cells. In some embodiments, the composition further comprises a cryopreservation medium. In some embodiments, the composition further comprises one or more agents that activate iNKT cells, e.g., α-GalCer or salts or esters thereof, α-GalCer-presenting dendritic cells, or artificial APCs.

In some embodiments, the present invention provides kits comprising one or more engineered cells or compositions according to the present invention packaged together with a drug delivery device, e.g., a syringe, for delivering the engineered cells or compositions to a subject. In some embodiments, the present invention provides kits comprising one or more engineered cells or compositions according to the present invention packaged together with one or more reagents for culturing and/or storing the engineered cells. In some embodiments, the present invention provides kits comprising one or more engineered cells or compositions according to the present invention packaged together with one or more agents that activate iNKT cells. In some embodiments, the present invention provides kits comprising one or more engineered cells or compositions according to the present invention packaged together with OP9-DL1 stromal cells and/or MS5-DL4 stromal cells. In some embodiments, the present invention provides kits comprising one or more engineered cells or compositions according to the present invention packaged together with antigen-presenting cells or CD1d-expressing artificial antigen-presenting cells.

In some embodiments, the present invention provides a method of treating a subject, which comprises administering to the subject one or more engineered cells according to the present invention, one or more engineered cells made according to a method of the present invention, or one or more compositions according to the present invention. In some embodiments, the subject is an animal such as a mouse or a test animal. In some embodiments, the subject is a human. In some embodiments, the subject is in need of treatment with iNKT cells. In some embodiments, the subject has a cancer, a bacterial infection, a viral infection, an allergy, or an autoimmune disease. In some embodiments, the cancer is melanoma, kidney cancer, lung cancer, prostate cancer, breast cancer, lymphoma, leukemia, or a hematological malignancy. In some embodiments, the subject has tuberculosis, HIV, or hepatitis. In some embodiments, the subject has asthma or eczema. In some embodiments, the subject has Type I diabetes, multiple sclerosis, or arthritis. In some embodiments, the subject is administered a therapeutically effective amount of the one or more engineered cells. In some embodiments, the therapeutically effective amount of the one or more engineered cells is about $10^7$ to about $10^9$ cells per kg body weight of the subject being treated. In some embodiments, the method further comprises administering an agent that activates iNKT cells, e.g., α-GalCer or salts or esters thereof, α-GalCer-presenting dendritic cells or artificial APCs, before, during, and/or after administration of the one or more engineered cells.

In some embodiments, the present invention provides medicaments and methods of making medicaments for treating subjects in need of treatment with iNKT cells, said medicaments comprise a therapeutically effective amount of one or more engineered cells according to the present invention. In some embodiments, the medicaments comprise a concentration of about $1.0 \times 10^5$ to about $1.0 \times 10^7$ cells/ml of a pharmaceutically acceptable carrier or diluent. In some embodiments, the medicaments comprise a concentration of about $1.0 \times 10^5$ to about $1.0 \times 10^6$ cells/ml of a pharmaceutically acceptable carrier or diluent. In some embodiments, the medicaments comprise a concentration of about $1.0 \times 10^6$ to about $1.0 \times 10^7$ cells/ml of a pharmaceutically acceptable carrier or diluent. In some embodiments, the medicaments can comprise a concentration that is higher than $1.0 \times 10^7$ cells/ml. In some embodiments, the medicaments comprise about $1 \times 10^7$ to about $1 \times 10^9$ of the one or more engineered cells. In some embodiments, the medicaments comprise about $1 \times 10^7$ to about $1 \times 10^8$ of the one or more engineered cells. In some embodiments, the medicaments comprise about $1 \times 10^8$ to about $1 \times 10^9$ of the one or more engineered cells.

In some embodiments, the present invention provides use of one or more engineered cells according to the present invention in the manufacture of a medicament for treating a subject in need of treatment with iNKT cells. In some embodiments, the medicaments comprise a therapeutically effective amount of the one or more engineered cells.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein (in the drawings, "HSC" refers to "HSPC"):

FIG. 1A shows a representative FACS plot. Single iNKT cells were sorted out from mouse spleen cells using flow cytometry based on a stringent collection of surface markers (gated as $CD3^{lo}mCD1d/PBS-57^+TCR$ $V\beta8^+NK1.1^{hi}$). mCD1d/PBS-57 indicates the tetramer reagent that specifically stains mouse iNKT TCRs.

FIG. 1B shows a representative DNA gel showing the TCR α and β chain gene PCR products from five iNKT cells. Sorted single iNKT cells were subjected to TCR cloning using a single-cell RT-PCR approach.

FIG. 1C shows representative sequencing results confirming the cloned single-cell iNKT TCR α and β chain genes. The top 5 sequences for iNKT TCRα are SEQ ID NO: 1, and for the iNKT TCR β sequences (the bottom 5 sequences), from top to bottom, the SEQ ID NOs are: SEQ ID NO: 2, SEQ ID NO: 3, SEQ ID NO: 4, SEQ ID NO: 5, and SEQ ID NO: 6.

FIG. 1D is a schematic representation of the retroviral vectors encoding either a control EGFP reporter gene (denoted as the Mock vector), or a pair of iNKT TCR α and β chain genes (denoted as the miNKT vector). LTR indicates long-term repeats; IRES, internal ribosome entry sites;

EGFP, enhanced green fluorescence protein; F2A, foot-and-mouth disease virus 2A sequence; and WRE, woodchuck responsive element.

Figure 1A:
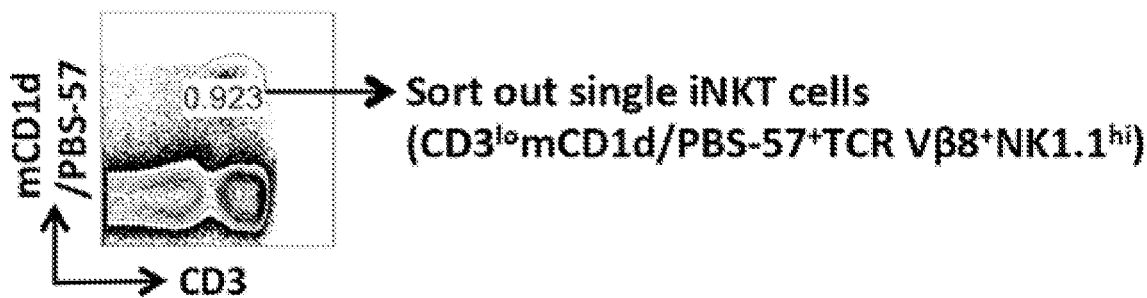
FIGS. 1A-1F schematically show the cloning of invariant natural killer T-cell receptor (iNKT TCR) genes, construction of retroviral delivery vectors, and expression of clonal iNKT TCRs.
Figure 1B:
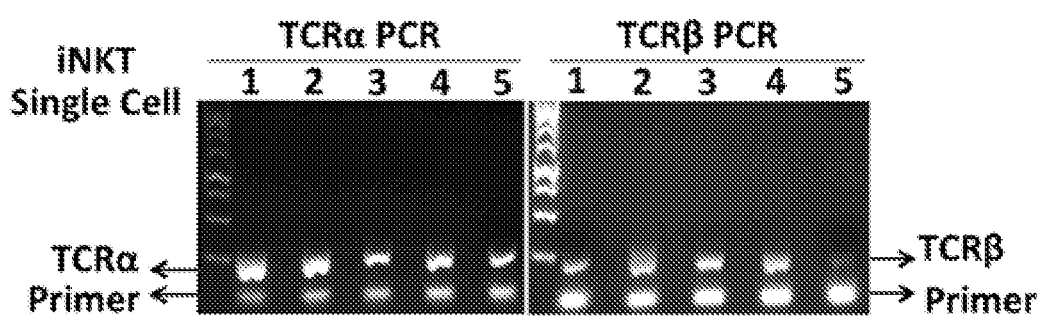
Figure 1C:
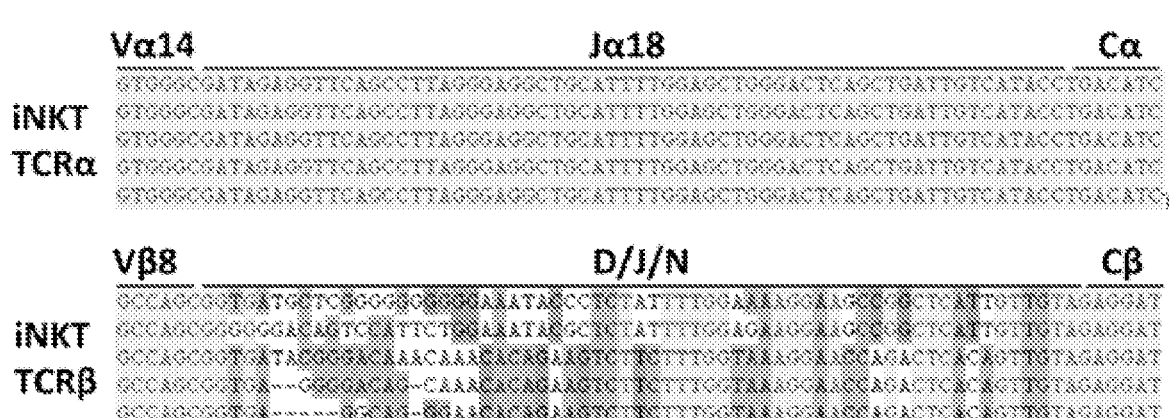
Figure 1D:
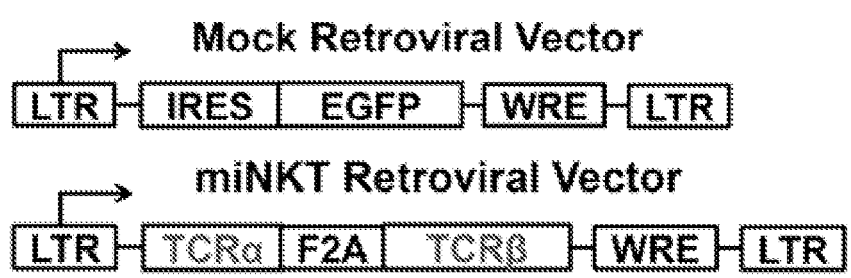
Figure 1E:
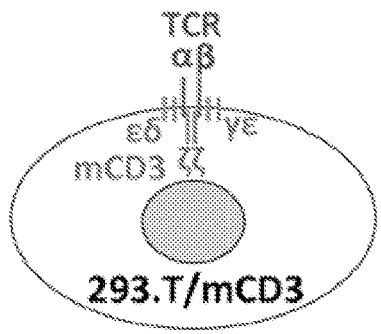

FIG. 1E is a schematic representation of the 293.T cell line that has been engineered to stably express mouse CD3 genes and so as to support the surface display of mouse TCRs (denoted as 293.T/mCD3).

Figure 1F:
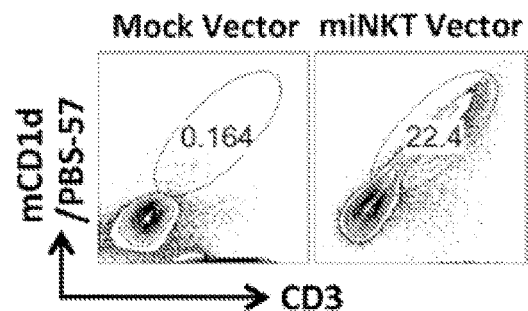

FIG. 1F are representative FACS plots showing the expression of clonal iNKT TCRs in 293.T/mCD3 cells transduced with the chosen miNKT vector.

FIGS. 2A-2K show the generation of functional iNKT cells through TCR gene engineering of hematopoietic stem cells (HSCs) and the characteristics of the HSPC-iNKT cells. B6 mice receiving adoptive transfer of HSCs transduced with either the Mock retroviral vector (denoted as B6-Mock mice) or miNKT retroviral vector (denoted as B6-miNKT mice) were allowed to reconstitute their immune system in a duration of 6-8 weeks, followed by analysis. The experiments were repeated at least three times, and representative results are presented. HSPC-iNKT cells were detected as TCRβ$^{lo}$mCD1d/PBS-57$^+$ using flow cytometry.

Figure 2A:
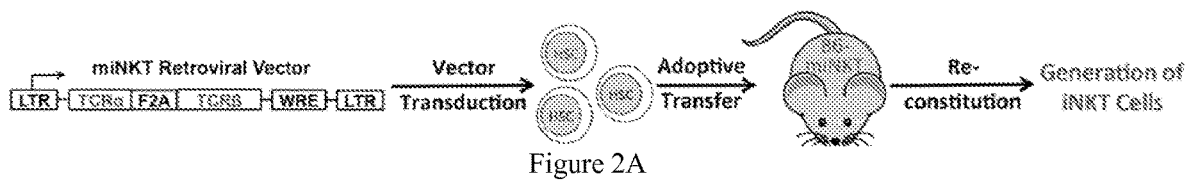

FIG. 2A is a schematic representation of the experimental design to generate HSPC-iNKT cells in mice.

Figure 2B:
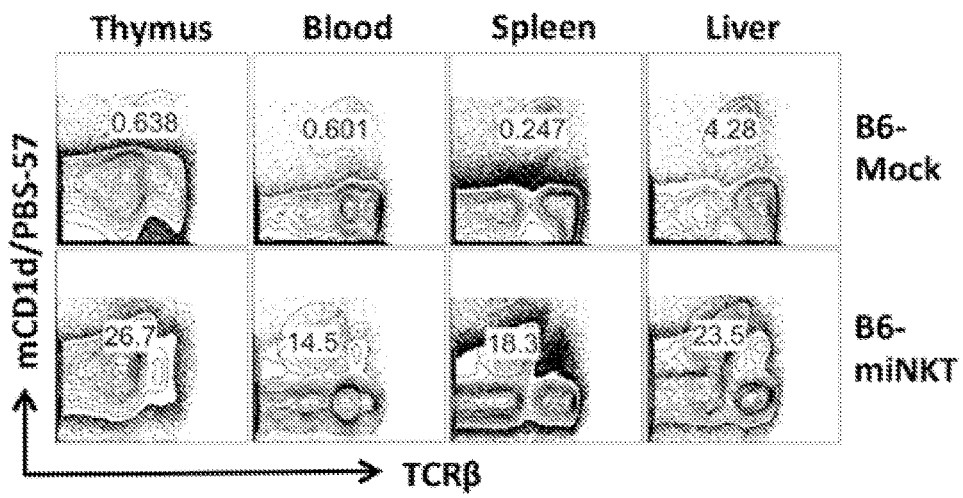
Figure 2C:
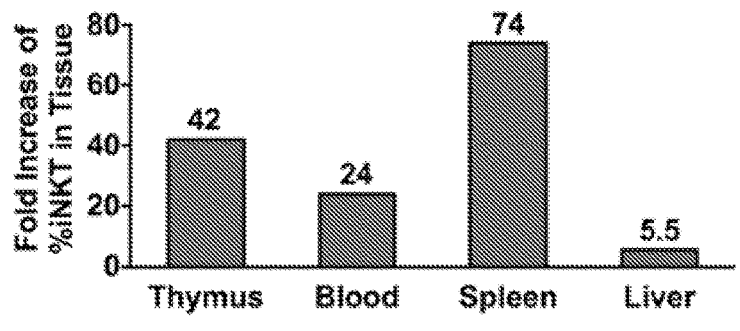

FIGS. 2B and 2C show an increase of iNKT cells in B6-miNKT mice compared with that in the control B6-Mock mice. FIG. 2B are FACS plots showing the detection of iNKT cells in various tissues. FIG. 2C are bar graphs showing the fold increase of percent iNKT cells in the indicated tissues.

FIGS. 2D and 2E show control of iNKT cell numbers in B6-miNKT mice through titrating the miNKT vector-transduced HSPCs used for adoptive transfer. FIG. 2D are FACS plots showing the detection of iNKT cells in the spleens of various B6-miNKT recipient mice. Tc indicates the conventional αβ T cells (gated as TCRβ$^+$mCD1d/PBS-57$^-$). FIG. 2E are bar graphs showing the percent iNKT of total αβ T cells in spleen.

FIG. 2F are FACS plots showing the phenotype of the HSPC-iNKT cells. FACS plots are presented showing the surface markers of iNKT cells detected in the liver of B6-miNKT mice.

FIGS. 2G and 2H show long-term production of HSPC-iNKT cells. FACS plots are presented showing the detection of HSPC-iNKT cells in the spleen of B6-miNKT mice for up to 6 months after initial HSPC adoptive transfer (FIG. 2G) and at 2 months after secondary bone marrow transfer (BMT) (FIG. 2H).

Figure 2I:
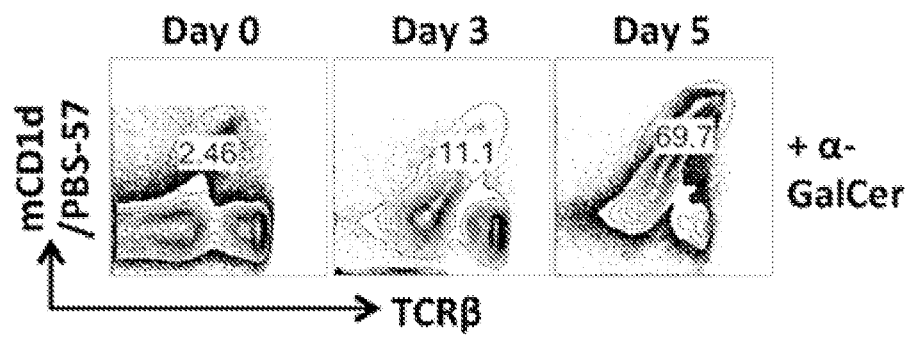
Figure 2J:
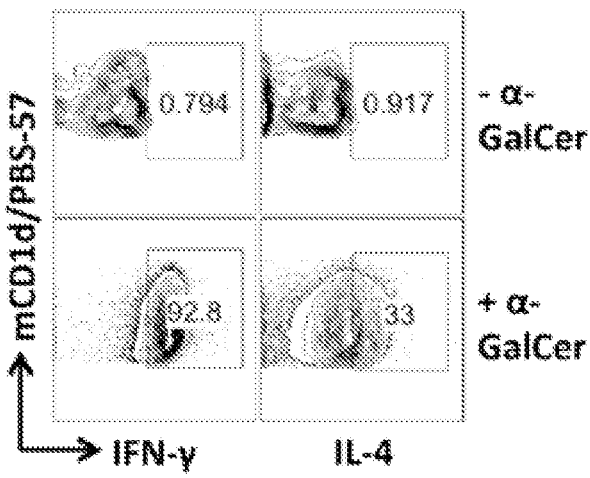
Figure 2K:
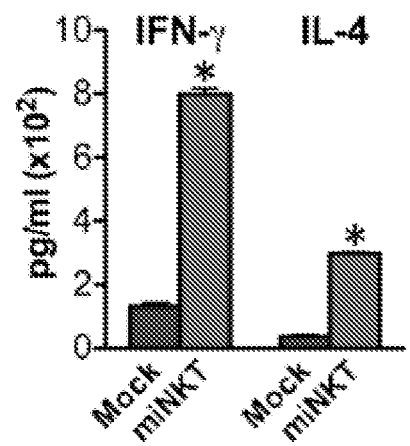

FIGS. 2I-2K show the functionality of the HSPC-iNKT cells tested in vitro. Spleen cells of B6-miNKT mice were cultured in vitro in the presence of α-GalCer (100 ng/mL). FIG. 2I are FACS plots showing the time-course proliferation of HSPC-iNKT cells. FIG. 2J are FACS plots showing the cytokine production in HSPC-iNKT cells on Day 3, as measured by intracellular cytokine staining. FIG. 2K are bar graphs of the ELISA analysis of cytokine production in the cell culture medium at Day 3. Data are presented as mean of duplicate cultures±SEM, *P<0.01 (B6-miNKT samples compared with the corresponding B6-Mock controls).

Figure 2L:
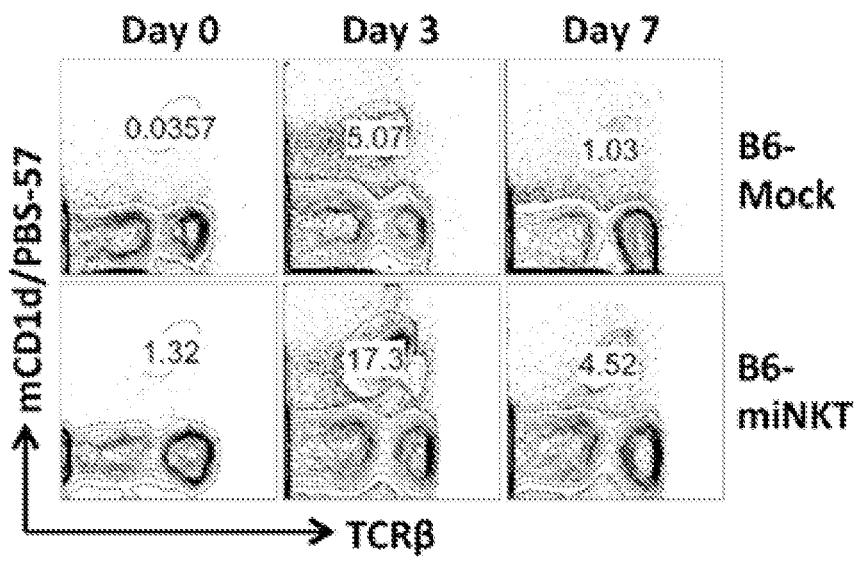

FIG. 2L are FACS plots showing the functionality of the HSPC-iNKT cells tested in vivo. B6-Mock or B6-miNKT mice were given i.v. injection of 1×10$^6$ bone marrow-derived dendritic cells (BMDCs) loaded with α-GalCer (denoted as BMDC/α-GalCer) and then periodically bled to monitor iNKT cell responses. FACS plots are presented showing the change of iNKT cell frequencies in blood.

FIGS. 3A-3E shows the development of the HSPC-iNKT cells. B6-miNKT and control B6-Mock mice were analyzed for iNKT cell development at 6-8 weeks post HSPC transfer. The experiments were repeated at least three times, and representative results are presented. HSPC-iNKT cells were detected as TCRβ$^{lo}$CD1d/PBS-57$^+$ using flow cytometry.

Figure 3A:
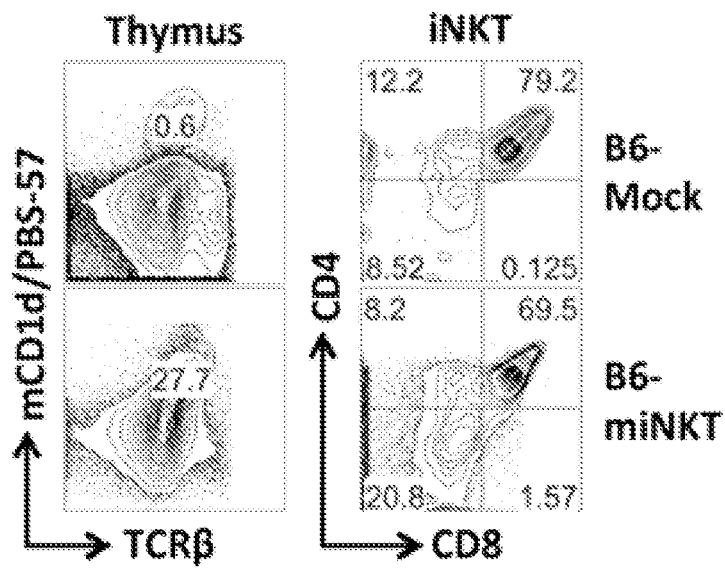
Figure 3B:
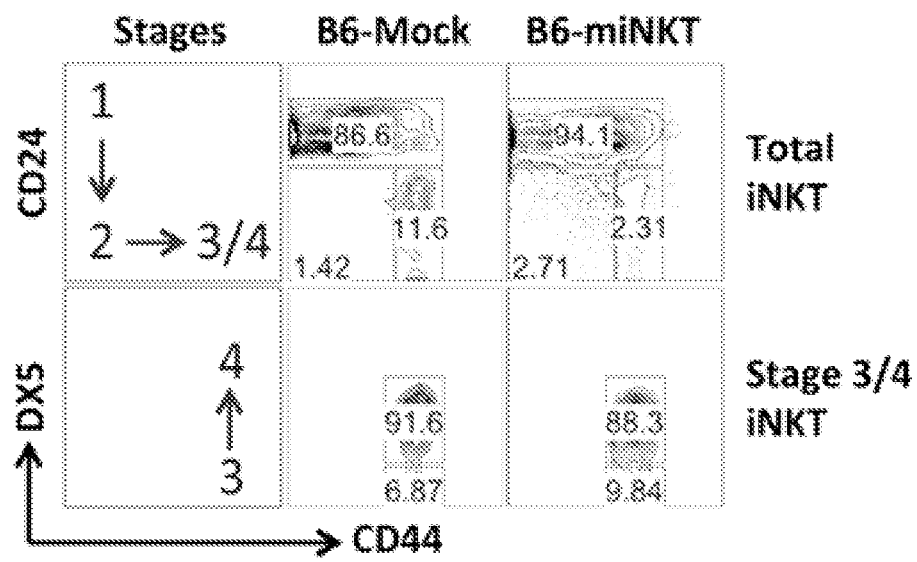

FIGS. 3A and 3B are FACS plots showing the characteristic development of HSPC-iNKT cells in thymus.

Figure 3C:
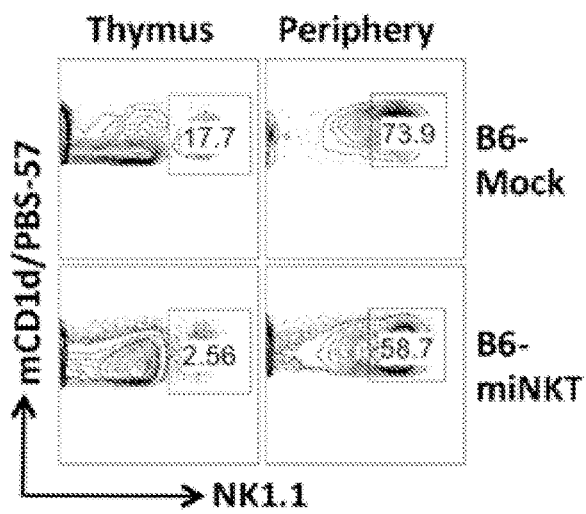

FIG. 3C are FACS plots showing the maturation of HSPC-iNKT cells in the periphery measured by the up-regulation of the NK1.1 marker. Comparisons of HSPC-iNKT cells from thymus and periphery (liver) are shown.

Figure 3D:
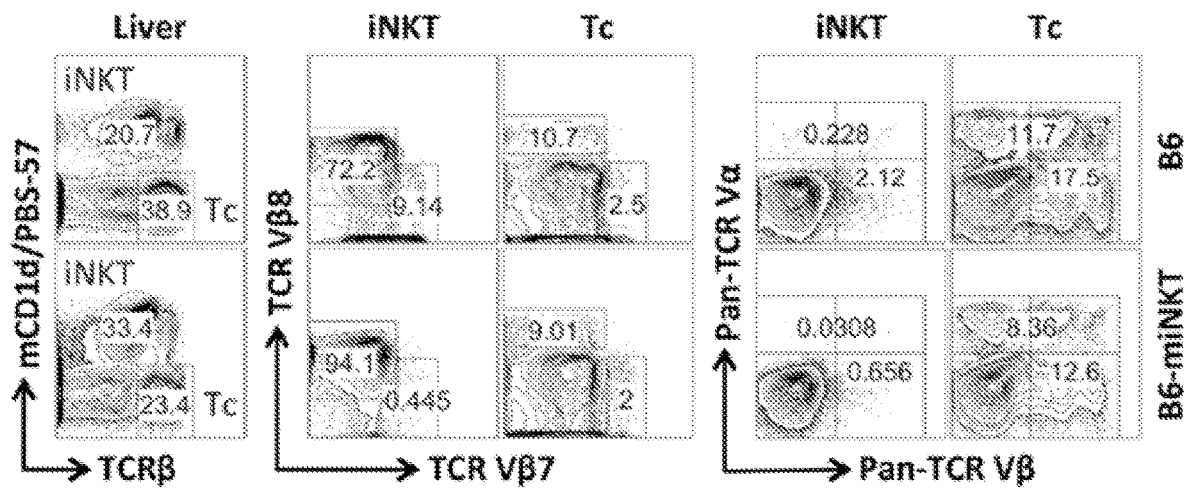
Figure 3E:
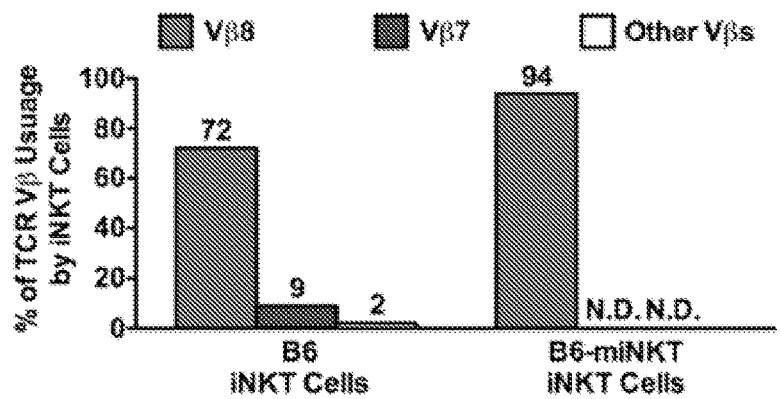

FIGS. 3D and 3E are FACS plots and bar graphs showing the exclusion of non-transgenic TCR expression on the HSPC-iNKT cells. Comparisons of iNKT and conventional αβ T (Tc) cells from the liver of B6-Mock or B6-miNKT mice are shown. Pan-TCR Vα panel includes Vα2, Vα3.2, and Vα8.3, whereas pan-TCR Vβ panel includes Vβ3, Vβ4, Vβ5, Vβ6, Vβ11, and Vβ13. N.D., not detected. As shown in FIG. 3E, the first bars of each set are Vβ8, the second bars of each set are Vβ7, and the third bars of each set are other Vβs.

FIGS. 4A-4F show protection from melanoma lung metastasis by the HSPC-iNKT cells. B6-miNKT and control B6-Mock mice were given i.v. injection of 0.5-1×10$^6$ B16.F10 melanoma cells on Day 0 and analyzed for melanoma lung metastasis on Day 14. On Day 3, experimental mice received i.v. injection of 1×10$^6$ BMDCs either unloaded or loaded with α-GalCer (denoted as BMDC/none or BMDC/α-GalCer, respectively) to mimic a therapeutic vaccine treatment. The experiments were repeated twice (5-7 mice per group), and representative results are presented.

Figure 4A:
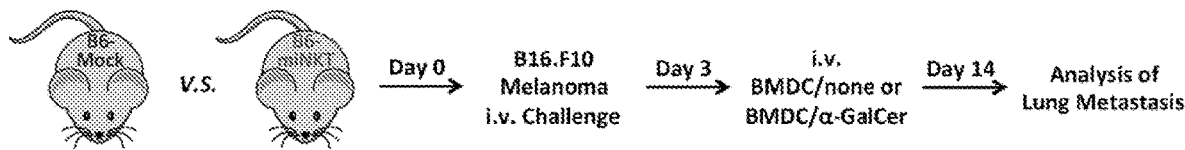

FIG. 4A is a schematic representation of the experimental design to study the cancer therapy potential of the HSPC-iNKT cells in the B16 melanoma lung metastasis mouse model.

Figure 4B:
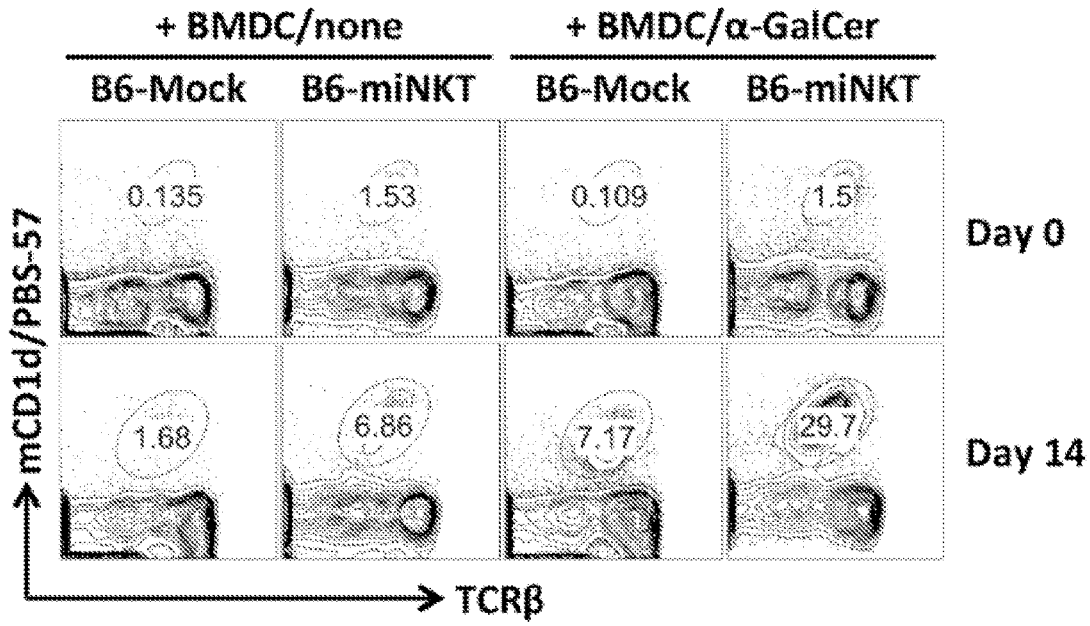

FIG. 4B are FACS plots showing the expansion of HSPC-iNKT cells in the blood of experimental mice in response to tumor challenge and BMDC/α-GalCer vaccination.

Figure 4C:
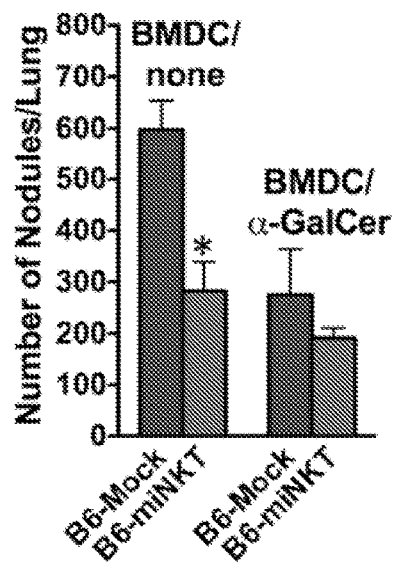
Figure 4D:
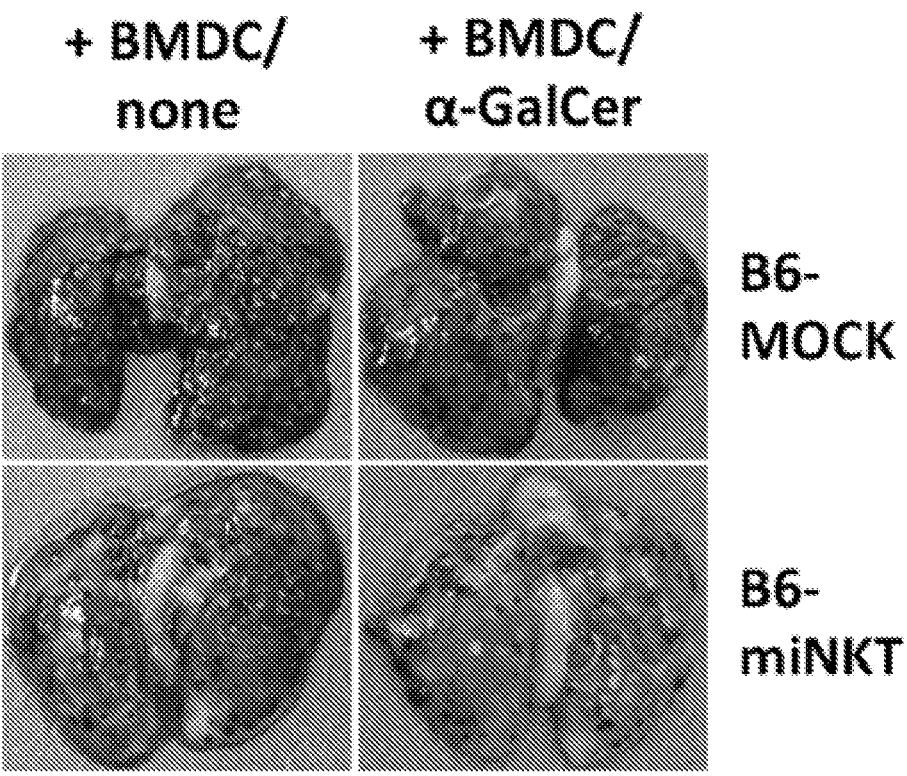
Figure 4E:
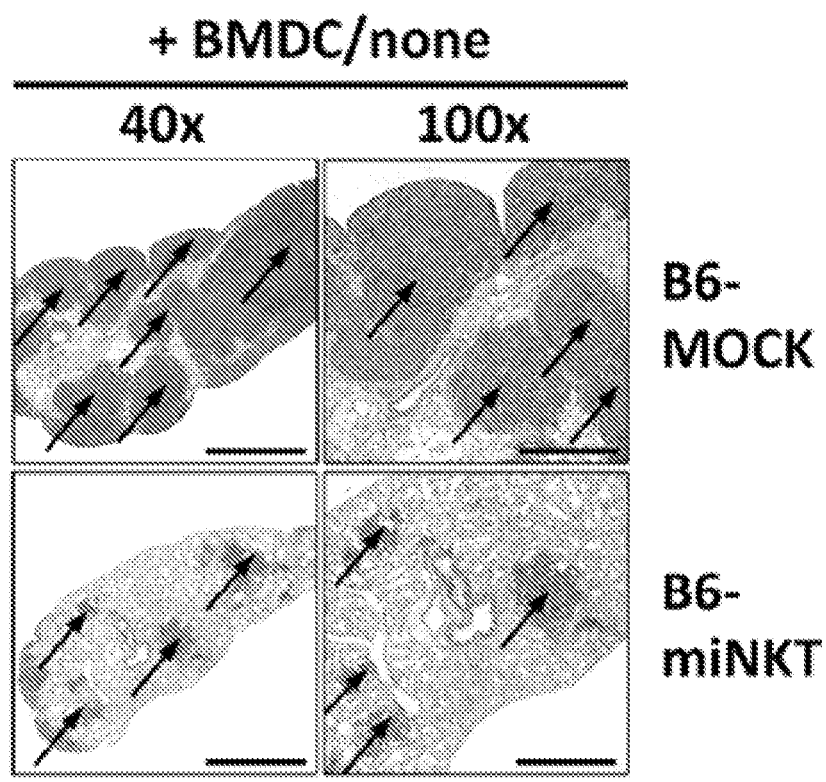
Figure 4F:
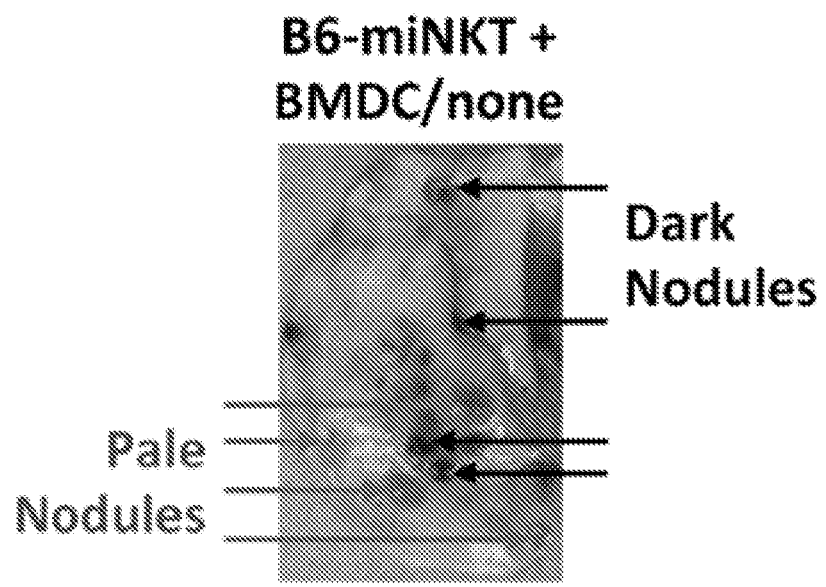

FIGS. 4C-4F show the analysis of melanoma lung metastasis in the experimental mice on Day 14. FIG. 4C is a bar graph showing the enumeration of lung tumor nodules. Data are presented as mean±SEM, *P<0.01 (B6-miNKT samples compared with corresponding B6-Mock controls). FIG. 4D are photos of lung showing melanoma metastasis. FIG. 4E are immunohistological lung sections with H-E staining. Metastatic tumor nodules are indicated by arrows. Bars: 1,000 μm (40× magnification); 500 μm (100× magnification). FIG. 4F is an image of a lung from a representative B6-miNKT mouse showing the detection of pale, depigmented tumor nodules.

Figure 5:
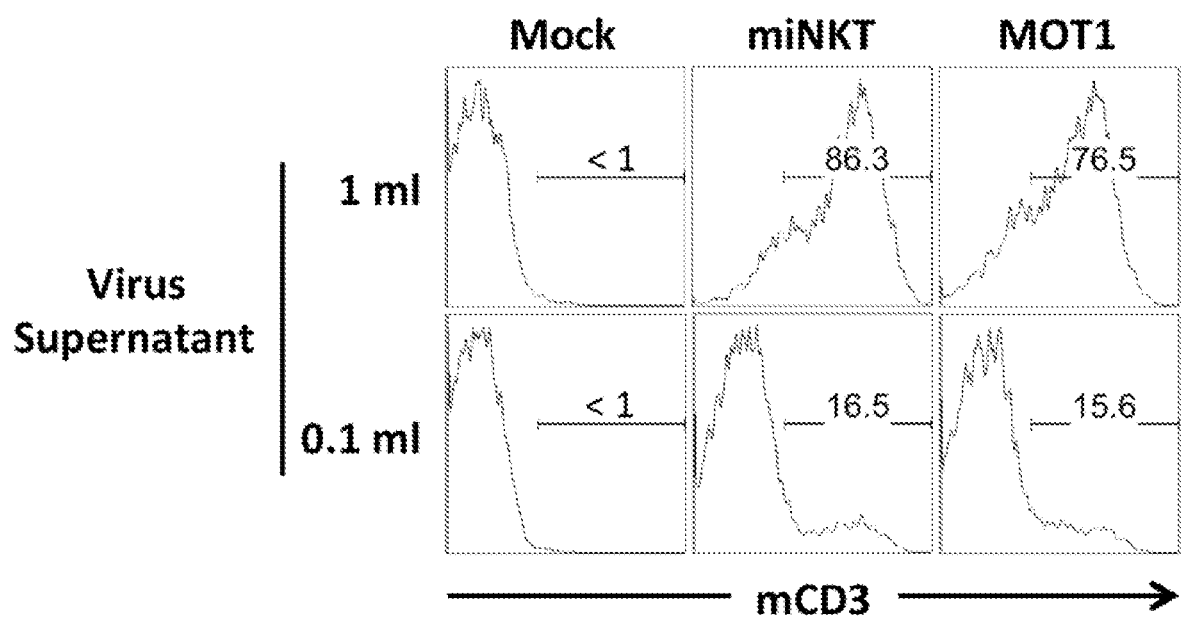

FIG. 5 are FACS plots showing the detection of mouse TCRs on cell surface. Titration of the miNKT retroviral vector. The 293.T/mCD3 cells were transduced with the titrated volume of indicated virus supernatants. Three days later, virus-mediated expression of mouse TCRs was measured using flow cytometry. Note mouse CD3 (mCD3) molecules only display on cell surface in complex with the transgenic mouse TCRs, therefore, they can be used as an indicator of transgenic TCR expression. The results show comparable titers of the miNKT and MOT1 retroviral vectors, estimated as about 0.5-1×10$^6$ IFU/mL (infectious units per milliliter). Mock, the control retroviral vector encoding an EGFP reporter gene; miNKT, the retroviral vector encoding a selected pair of mouse iNKT TCR α and β chain genes; MOT1, the retroviral vector encoding the α and β chain genes of OT1 TCR, a mouse conventional αβ TCR specific for chicken ovalbumin.

Figure 6A:
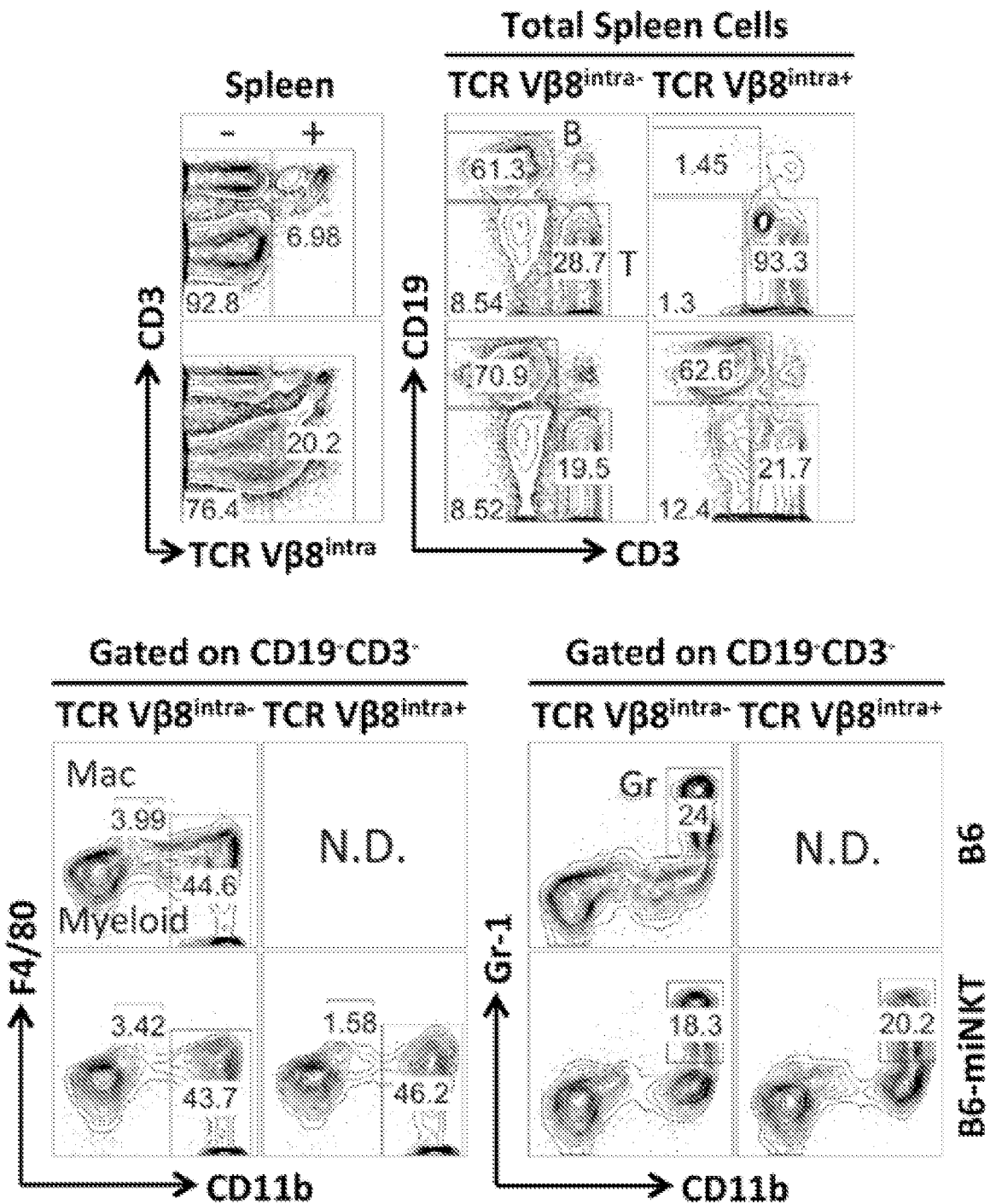
Figure 6B:
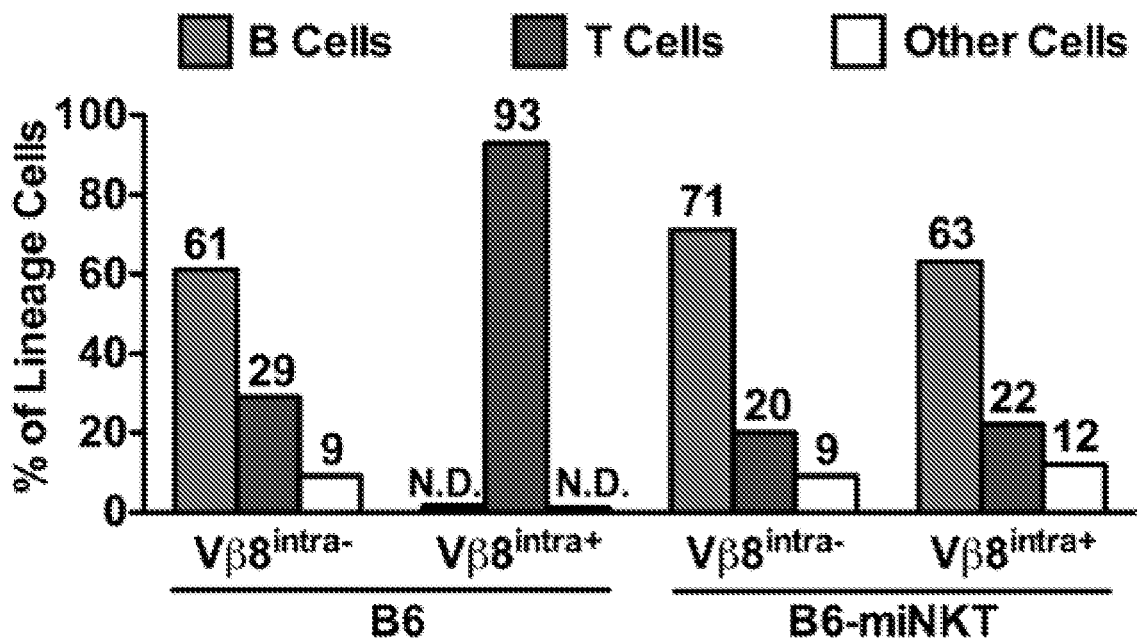

FIGS. 6A and 6B show lineage differentiation of TCR-transduced HSPCs. B6-miNKT and control B6-Mock mice were analyzed for the presence of HSPC-iNKT cells at 6-8 weeks post HSPC transfer. The experiments were repeated at least three times, and representative FACS plots (FIG. 6A) and bar graphs (FIG. 6B) are shown. Engineered cells were detected by intracellular staining of the transgenic TCRβ chain (gated as TCR Vβ8$^{intra+}$). Comparison analysis of the spleen cells of B6-miNKT and B6 control mice is presented. N.D., not detected. In the bar graphs, the first bars in each set are B cells, the second bars in each set are T cells, and the third bars in each set are other cells.

Figure 7A:
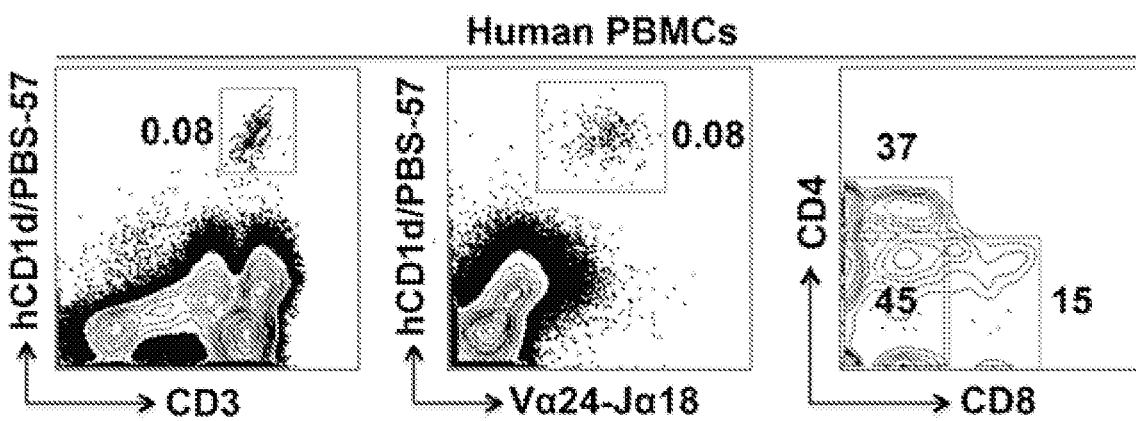
Figure 7B:
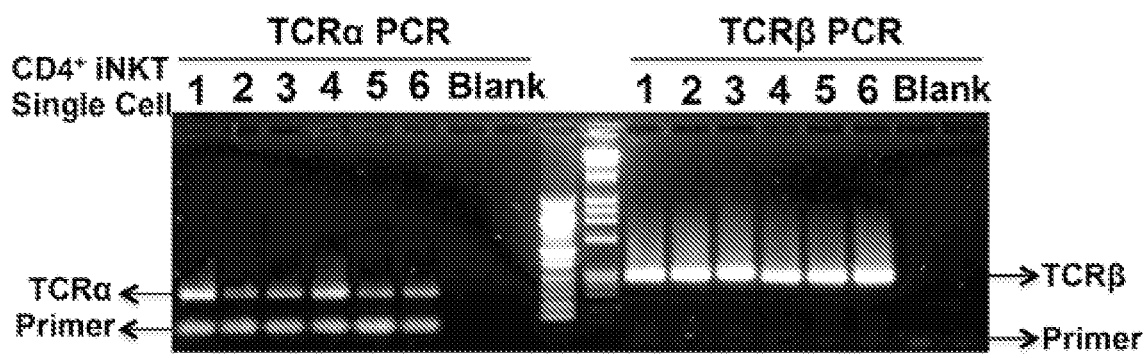
Figure 7C:
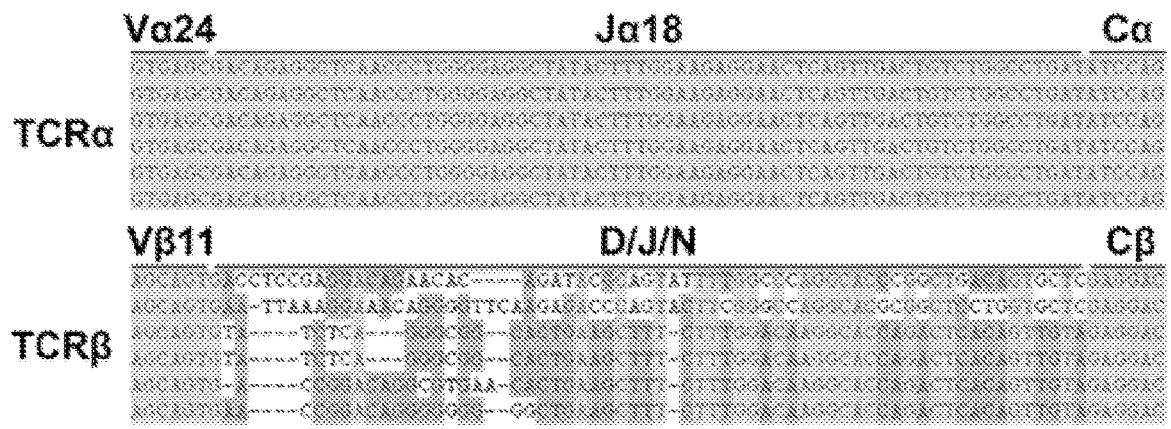

FIGS. 7A-7C schematically show the cloning of human iNKT TCR genes.

FIG. 7A shows flow cytometry analysis to detect human iNKT cells (gated as CD3$^{lo}$hCD1d/PBS-57$^+$Vα24-Jα18$^+$) and their CD4/CD8/DN subsets (gated as CD4$^+$CD8$^-$, CD4$^-$CD8$^+$ or CD4$^-$CD8$^-$, respectively) in PBMCs.

FIG. 7B is a gel image showing the TCRα and TCRβ PCR products from 6 CD4$^+$ iNKT single cells. Single-cell RT-PCR was to clone iNKT TCRs.

FIG. 7C show the sequencing results of the PCR products, showing an invariant TCRα (Vα24-Jα18) and semi-invariant TCRβ (Vβ11 joined with varied D/J/N segments). The top 6 sequences for iNKT TCRα are SEQ ID NO: 7, and for the iNKT TCR β sequences (the bottom 6 sequences), from top to bottom, the SEQ ID NOs are: SEQ ID NO: 8, SEQ ID NO: 9, SEQ ID NO: 10, SEQ ID NO: 11, SEQ ID NO: 12, and SEQ ID NO: 13.

Figure 8A:
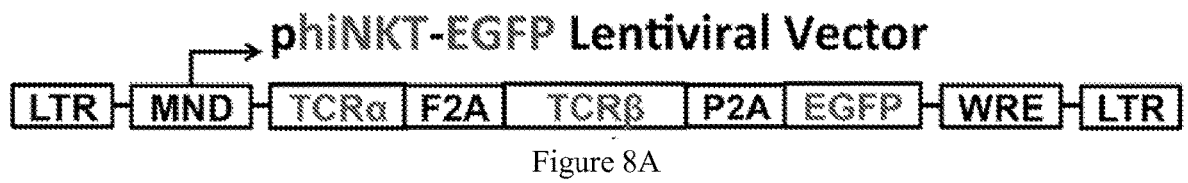
Figure 8B:
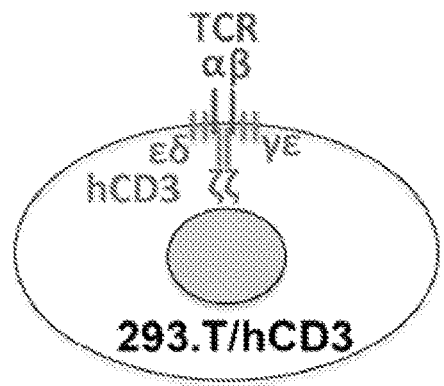
Figure 8C:
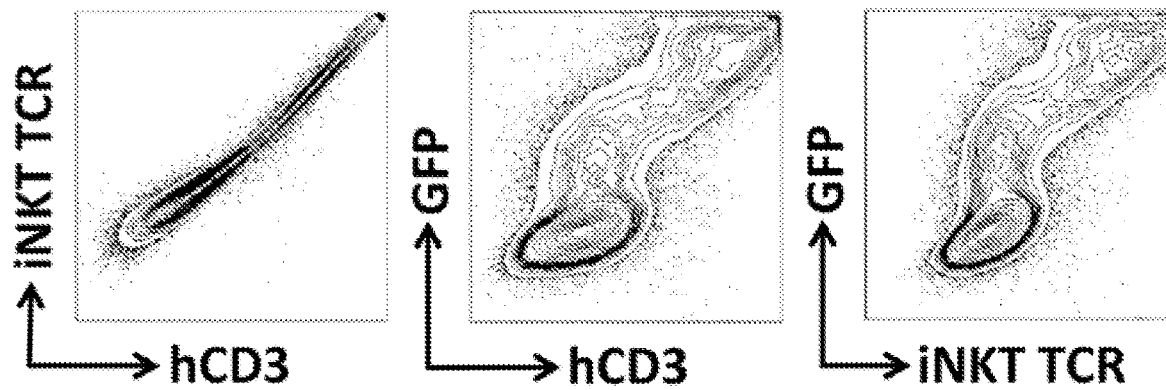

FIGS. 8A-8C schematically show the construction of human iNKT TCR delivery lentivectors. Construction of lentiviral vectors delivering human iNKT TCR genes.

FIG. 8A is a schematic representation of the phiNKT-EGFP lentivector. LTR: long-term repeats; MND: synthetic MND promoter; F2A: foot-and-mouth disease virus 2A sequence; P2A: porcine teschovirus-1 2A sequence; EGFP: enhanced green fluorescence protein; WRE: woodchuck responsive element.

FIG. 8B schematically shows the 293.T/hCD3 stable cell line used to test human TCR expression.

FIG. 8C shows flow cytometry analysis of GFP and surface expression of human iNKT TCRs in 293.T/hCD3 cells transduced with a representative phiNKT-EGFP lentivector.

Figure 9A:
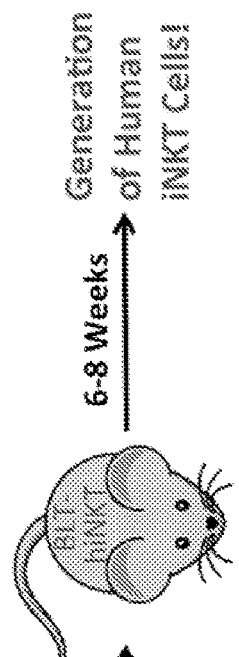
Figure 9A:
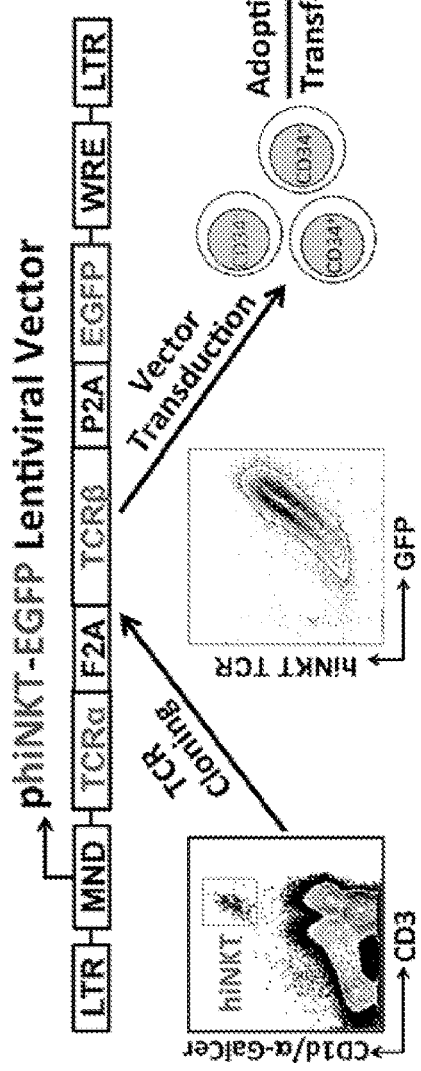
Figure 9B:
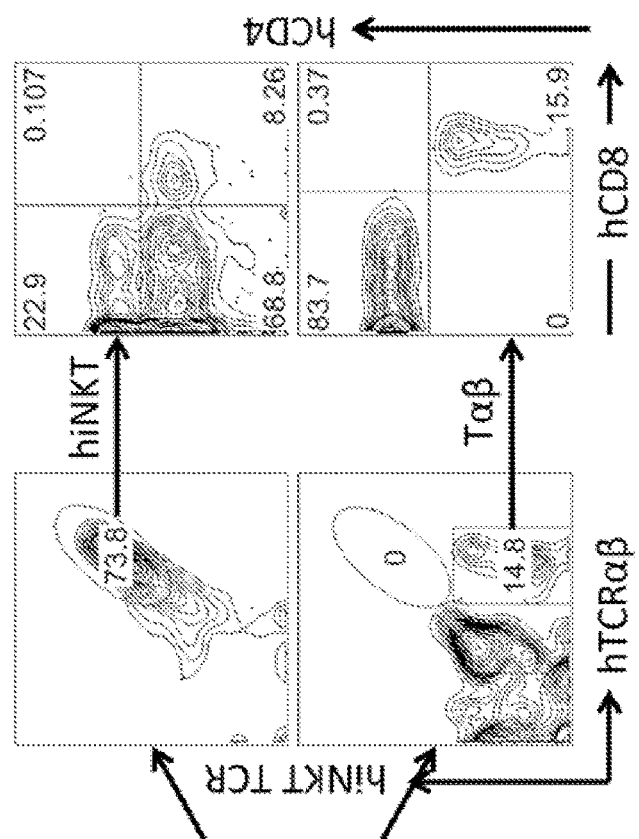
Figure 9B:
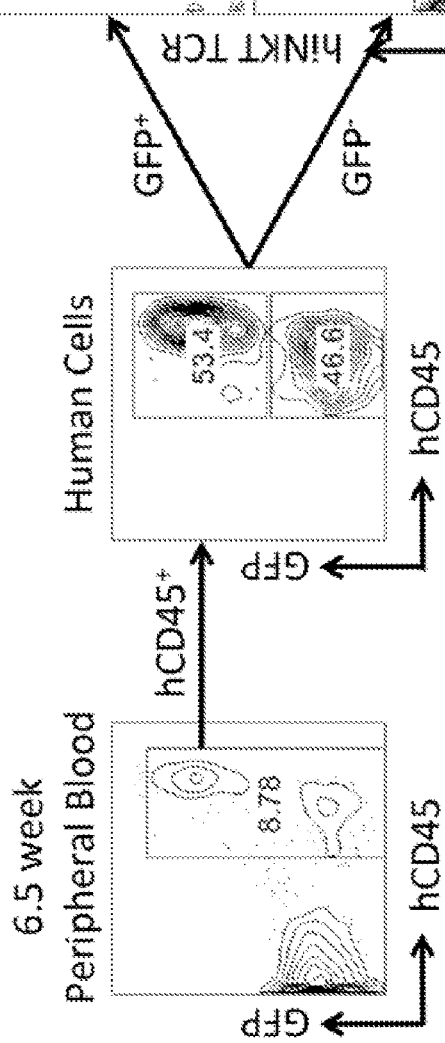

FIGS. 9A and 9B schematically show the generation of HSPC-iNKT cells and successful generation of HSPC-iNKT cells in BLT humanized mice.

FIG. 9A is a schematic of the experimental design to generate human HSPC-iNKT cells according to the present invention.

FIG. 9B show the successful detection of HSPC-iNKT cells in the peripheral blood of BLT-hiNKT mice 6.5 weeks post CD34$^+$ cell adoptive transfer.

DETAILED DESCRIPTION OF THE INVENTION

The present invention provides "HSPC-iNKT cells", invariant natural killer T (iNKT) cells engineered from hematopoietic stem cells (HSCs) and/or hematopoietic progenitor cells (HPCs), and methods of making and using thereof. As used herein, "HSPCs" is used to refer to HSCs, HPCs, or both HSCs and HPCs. The methods for making HSPC-iNKT cells according to the present invention are cost-effective and high-throughput. For example, using the methods of the present invention, one can readily implement retrovirus-transduced bone marrow transfer and generate HSPC-iNKT cells within as few as 6 weeks.

As disclosed herein, large numbers of HSPC-iNKT cells were generated by transducing HSPCs with one or more nucleic acid sequences encoding iNKT T cell receptors (TCRs) and engrafting the TCR-transduced HSPCs in subjects. Once engrafted, the transduced cells follow a two-stage developmental path, first in thymus and then in the periphery, which resembles that of endogenous iNKT cells and results in functional HSPC-iNKT cells. When tested in a mouse melanoma lung metastasis model, the HSPC-iNKT cells effectively protected mice from tumor metastasis.

HSPC-iNKT cells according to the present invention can also be generated in vitro. For example, HSPCs can be transduced with one or more iNKT TCR nucleic acid sequences and cultured with OP9-DL1 or MS5-DL4 stromal cells (Sun, et al. (2015) Cytokine 72:48-57) to result in TCR-engineered iNKT cells. The resulting iNKT cells can be further expanded by secondary culture with irradiated donor peripheral blood mononuclear cells (PBMCs) as antigen-presenting cells (APCs) or CD1d-expressing artificial antigen-presenting cells (aAPCs) in the presence of agonist antigen like α-galactosylceramide (α-GalCer). An example of such aAPCs could be K562 cells engineered to overexpress CD1d (Tian, et al. (2013) J. Immunol. 190:45.3).

As disclosed herein, HSPC-iNKT cells according to the present invention follow a classical iNKT cell development path, Check Point 1 in the thymus to gain iNKT TCR expression and Check Point 2 in the periphery to gain NK1.1 expression. They also display a typical iNKT cell phenotype (TCRβ$^{lo}$mCD1d/PBS-57$^{hi}$NK1.1$^{hi}$CD62L$^{lo}$CD44$^{hi}$CD4$^{+/-}$CD8$^-$) and exhibit full iNKT cell functionality with potent and fast response to antigen stimulation, both in vitro and in vivo. Thus, the HSPC-iNKT cells according to the present invention are functional, which means the HSPC-iNKT cells are able to produce, upon activation, one or more cytokines and/or chemokines such as IFNγ, TNFα, TGFβ, GM-CSF, IL-2, IL-4, IL-5, IL-6, IL-10, IL-13, IL-17, IL-21, RANTES, Eotaxin, MIP-1α, MIP-1β, and the like.

Because the HSPC-iNKT cells of the present invention are functional, they can be used to study iNKT cell biology. The development and function of HSPC-iNKT cells in healthy and disease conditions can be monitored by varying the levels of HSPC-iNKT cells in subjects. In addition, using the methods of the present invention, one can generate large numbers of clonal HSPC-iNKT cells and thereby investigate the similarities and differences between individual iNKT cell clones. For example, by studying the antigen recognition and functional differentiation of single iNKT cell clones, important clues might be revealed to increase understanding of the origins of various iNKT cell subsets with distinct functions, such as those iNKT cell subsets biased to produce Th1, Th2, or Th17 effector cytokines. The flexibility of the inventive methods also allow the convenient generation of HSPC-iNKT cells of different genomic backgrounds at a fast pace and an affordable cost, allowing examination of the functions of designated genes for regulating iNKT cell biology.

HSPC-iNKT cells according to the present invention can be used in a variety of therapeutic treatments. Unlike transgenic mouse technologies, the inventive methods can be applied to humans through gene-modified CD34$^+$ cell transfer and therefore can be used as therapeutics to treat a wide variety of diseases and disorders in humans. In addition, unlike iPS-derived iNKT cells, HSPC-iNKT cells according to the present invention do not contain exogenous oncogenes, such as Oct4, Sox2, Klf4, and c-Myc. Consequently, HSPC-iNKT cells of the present invention do not pose the same risks as iPS-derived iNKT cells when used to treat subjects. Therefore, the methods and HSPC-iNKT cells of the present invention can be used to provide subjects with a lifelong supply of iNKT cells. HSPC-iNKT cells according to the present invention can be used to treat various cancers such as melanoma, kidney cancer, lung cancer, prostate cancer, breast cancer, lymphoma, leukemia, and hematological malignancies, bacterial and viral infections such as tuberculosis, HIV, hepatitis, allergies such as asthma and eczema, and autoimmune diseases such as Type I diabetes, multiple sclerosis, and arthritis.

Donor HSPCs can be obtained from the bone marrow, peripheral blood, amniotic fluid, or umbilical cord blood of a donor. The donor can be an autologous donor, i.e., the subject to be treated with the HSPC-iNKT cells, or an allogenic donor, i.e., a donor who is different from the subject to be treated with the HSPC-iNKT cells. In embodiments where the donor is an allogenic donor, the tissue (HLA) type of the allogenic donor preferably matches that of the subject being treated with the HSPC-iNKT cells derived from the donor HSPCs.

According to the present invention, an HSPC is transduced with one or more exogenous iNKT TCR nucleic acid molecules. As used herein, an "iNKT TCR nucleic acid molecule" is a nucleic acid molecule that encodes an alpha chain of an iNKT T cell receptor (TCRα), a beta chain of an iNKT T cell receptor (TCRβ), or both. As used herein, an "iNKT T cell receptor" is one that is expressed in an iNKT cell and recognizes α-GalCer presented on CD1d. The TCRα and TCRβ sequences of iNKT TCRs can be cloned and/or recombinantly engineered using methods in the art. For example, an iNKT cell can be obtained from a donor and the TCR α and β genes of the iNKT cell can be cloned as described herein. The iNKT TCR to be cloned can be obtained from any mammalian including humans, non-human primates such monkeys, mice, rats, hamsters, guinea pigs, and other rodents, rabbits, cats, dogs, horses, bovines, sheep, goat, pigs, and the like. In some embodiments, the iNKT TCR to be cloned is a human iNKT TCR. In some embodiments, the iNKT TCR clone comprises human iNKT TCR sequences and non-human iNKT TCR sequences.

In some embodiments, the cloned TCR can have a TCRα chain from one iNKT cell and a TCRβ chain from a different iNKT cell. In some embodiments, the iNKT cell from which the TCRα chain is obtained and the iNKT cell from which the TCRβ chain is obtained are from the same donor. In some embodiments, the donor of the iNKT cell from which the TCRα chain is obtained is different from the donor of the iNKT cell from which the TCRβ chain is obtained. In some embodiments, the sequence encoding the TCRα chain and/or the sequence encoding the TCRβ chain of a TCR clone is modified. In some embodiments, the modified sequence may encode the same polypeptide sequence as the unmodified TCR clone, e.g., the sequence is codon optimized for expression. In some embodiments, the modified sequence may encode a polypeptide that has a sequence that is different from the unmodified TCR clone, e.g., the modified sequence encodes a polypeptide sequence having one or more amino acid substitutions, deletions, and/or truncations.

The cloned and/or recombinantly engineered iNKT TCRα and TCRβ chains are then inserted into one or more expression vectors to give TCR expression vectors. In some embodiments, the cloned and/or recombinantly engineered iNKT TCRα and TCRβ chains are provided in the same expression vector and are functionally linked to result in their co-expression. In some embodiments, the expression vector is a retroviral vector or a lentiviral vector.

The donor HSPCs are then transduced with one or more TCR expression vectors. In some embodiments, an HSPC is transduced with a first TCR expression vector that encodes an iNKT TCRα chain and a second TCR expression vector that encodes a TCRβ chain. In some embodiments, an HSPC is transduced with a TCR expression vector that encodes both an iNKT TCRα chain and an iNKT TCRβ chain. In some embodiments, expression of the iNKT TCRα chain and the iNKT TCRβ chain are under the same promotor in one TCR expression vector. In some embodiments, expression of the iNKT TCRα chain is under a first promotor and the expression of the iNKT TCRβ chain is under a second promotor in one TCR expression vector. In some embodiments, the TCR-transduced HSPCs are expanded in vitro. In some embodiments, the TCR-transduced HSPCs are engrafted in a subject to generate clonal populations of HSPC-iNKT cells. In some embodiments, the subject is in need of treatment with iNKT cells. As used herein, a subject "in need of" treatment with iNKT cells is one who suffers from a condition that may be treated, reduced, or alleviated by increasing the number of iNKT cells in the subject. Examples of such conditions include cancers such as melanoma, kidney cancer, lung cancer, prostate cancer, breast cancer, lymphoma, leukemia, and hematological malignancies, bacterial infections such as tuberculosis, viral infections such as HIV and hepatitis, and allergies and autoimmune diseases such as asthma, eczema, Type I diabetes, multiple sclerosis, and arthritis. In some embodiments, the subject is a host subject having thymus tissue suitable for thymic development of the TCR-transduced HSPCs into HSPC-iNKT cells. In some embodiments, the host subject is a BLT mouse, e.g., a mouse surgically implanted with human thymus tissue. In some embodiments, HSPC-iNKT cells are obtained from a host subject. In some embodiments, HSPC-iNKT cells obtained from a host subject are administered to a subject in need of treatment with iNKT cells.

In some embodiments, TCR-transduced HSPCs are cultured in vitro, e.g., with OP9-DL1 or MS5-DL4 stromal cells, to give rise to HSPC-iNKT cells, which are capable of expressing one or more cytokines and/or chemokines upon activation. These engineered iNKT cells can be administered to a subject in need of treatment with iNKT cells. In some embodiments, these engineered iNKT cells can be further expanded by secondary culture with irradiated donor PBMCs as antigen-presenting cells (APCs) or CD1d-expressing artificial antigen-presenting cells (aAPCs) in the presence of agonist antigen like α-GalCer, which can then be administered to a subject in need of treatment with iNKT cells.

In some embodiments, the HSPC-iNKT cells are activated ex vivo for utilization as, for example, a source of active iNKT cells for immunotherapy. Therefore, in some embodiments, the present invention is directed to methods for generating active HSPC-iNKT cells by contacting HSPC-iNKT cells with anti-CD3/CD28, PMA/Ionomycin, or α-GalCer presented by cells such as PBMCs, dendritic cells (DCs), and artificial APCs. When the DC-activated HSPC-iNKT cells are intended to be administered to humans, the α-GalCer used to pulse DCs is desirably of GMP grade. Pulsation of DCs with α-GalCer can be performed by methods in the art; for example, the pulsation can be performed by culturing the DCs in a serum-containing medium (for example, 10% FCS-containing RPMI-1640 medium and the like) containing α-GalCer at a concentration of about 0.01 to about 5 μg/mL for about 2 to about 48 hours. In some embodiments, the pulsation with α-GalCer may be performed by adding α-GalCer to the medium in the process of culturing and maturing the immature DC in the presence of GM-CSF (and IL-4), or post DC maturation induced by LPS-treatment. In some embodiments, the pulsation may be performed by adding α-GalCer to the medium in the step of co-culturing the DC matured as described below with HSPC-iNKT cells. As used herein, an "active" or "activated" HSPC-iNKT cell refers to a HSPC-iNKT cell that at least produces a Th1 cytokine such as IFN-γ in response to α-GalCer-presenting DC. The cell may further be capable of producing a Th2 cytokine such as IL-4 and/or be capable of proliferating.

TCR-transduced HSPCs and/or HSPC-iNKT cells according to the present invention may be locally or systemically administered to subjects. In some embodiments, the present invention provides compositions comprising TCR-transduced HSPCs and/or HSPC-iNKT cells according to the present invention. In some embodiments, the compositions comprising TCR-transduced HSPCs and/or HSPC-iNKT cells according to the present invention are formulated for injection, suspension, or drip infusion, by being blended with a pharmaceutically acceptable carrier. In some embodiments, the compositions of the present invention comprise TCR-transduced HSPCs and/or HSPC-iNKT cells suspended in a pharmaceutically acceptable carrier at a concentration of about $1.0 \times 10^5$ to $1.0 \times 10^7$ cells/ml. The term "pharmaceutically acceptable carrier" as used herein refers to a carrier or diluent, which are added to a composition by the hand of a human, which is generally non-toxic to an intended recipient, does not significantly inhibit the activity of the TCR-transduced HSPCs and/or HSPC-iNKT cells, and is not cytotoxic to the TCR-transduced HSPCs and/or HSPC-iNKT cells. Pharmaceutically acceptable carriers include physiological saline and isotonic solutions containing glucose or another auxiliary drug (e.g., D-sorbitol, D-mannitol, sodium chloride and the like). In some embodiments, compositions according to the present invention may include one or more excipients, diluents, auxiliaries, preservatives, solubilizing agents, buffers, thickening agents, gelling agents, foaming agents, surfactants, binders, suspending agents, disintegrating agents, wetting agents, solvents, plasticizers, fillers, colorants, dispersants, and the like. In some embodiments, the compositions further comprise an agent that activates the HSPC-iNKT cells, e.g., α-GalCer or salts or esters thereof, α-GalCer-presenting dendritic cells, or artificial APCs.

In some embodiments, a therapeutically effective amount of one or more of the TCR-transduced HSPCs and/or HSPC-iNKT cells according to the present invention are administered to a subject. The term "therapeutically effective amount" as used herein is intended to mean an amount which is effective to alleviate, ameliorate, or prevent a symptom or sign of a disease or condition to be treated.

The amount of a composition of the present invention administered to a subject and the route of administration depends on factors such as the severity of an infection affecting the subject, the activity and rate of clearance/proliferation of the TCR-transduced HSPCs and/or HSPC-iNKT cells, and the general physical characteristics of the subject including age, gender, and body weight. One of skill in the art may readily determine a therapeutically effective amount and route of administration in view of these and other considerations typical in medical practice. Therapeutically effective amounts of one or more TCR-transduced HSPCs and/or HSPC-iNKT cells according to the present invention may be readily determined by those skilled in the art without undue experimentation.

In general, a therapeutically effective amount of one or more TCR-transduced HSPCs and/or HSPC-iNKT cells is about $10^7$ to about $10^9$ cells per kg body weight of the subject being treated. A therapeutically effective amount of one or more TCR-transduced HSPCs and/or HSPC-iNKT cells according to the present invention may be manufactured and/or administered in single or multiple unit dose forms. In some embodiments, the one or more TCR-transduced HSPCs and/or HSPC-iNKT cells are provided as a composition having a concentration of about $1.0 \times 10^5$ to about $1.0 \times 10^7$ cells/ml of a pharmaceutically acceptable carrier or diluent. In some embodiments, the composition comprises about $1 \times 10^7$ to about $1 \times 10^9$ of the one or more TCR-transduced HSPCs and/or HSPC-iNKT cells. In some embodiments, the composition comprises about $1 \times 10^7$ to about $1 \times 10^8$ of the one or more TCR-transduced HSPCs and/or HSPC-iNKT cells. In some embodiments, the composition comprises about $1 \times 10^8$ to about $1 \times 10^9$ of the one or more TCR-transduced HSPCs and/or HSPC-iNKT cells. In some embodiments, a subject is administered an agent that activates the HSPC-iNKT cells, e.g., α-GalCer or salts or esters thereof, α-GalCer-presenting dendritic cells before, during, and/or after administration of the one or more TCR-transduced HSPCs and/or HSPC-iNKT cells.

The following examples are intended to illustrate but not to limit the invention.

Examples

Cloning of iNKT TCR Genes and Construction of Retroviral Delivery Vectors

Disclosed herein is a robust and high-throughput single-cell TCR cloning method for obtaining iNKT TCR genes. Briefly, single iNKT cells were sorted from mouse spleen cells using flow cytometry based on a stringent collection of surface markers gated as $CD3^{lo}mCD1d/PBS-57^+TCR\ V\beta8^+$ NK1.1$^+$ (See FIG. 1A). mCD1d/PBS-57 is the tetramer reagent that specifically identifies iNKT TCRs. TCR Vβ8 staining was used to focus on the dominant Vβ8$^+$ population of mouse iNKT cells. The sorted single iNKT cells were then subjected to TCR cloning (See FIG. 1B). Several verified iNKT TCR α and β pairs were inserted into the murine stem cell virus (MSCV)-based retroviral vector to yield TCR gene delivery vectors (See FIG. 1C and FIG. 1D). Their vector-mediated expressions were then tested in 293.T/mCD3, a stable cell line engineered to express mouse CD3 molecules that support the surface display of mouse TCRs (See FIG. 1E). One vector, which mediated high expression of a high-affinity iNKT TCR, was selected for the follow-up studies and was denoted as the miNKT vector (See FIG. 1D and FIG. 1F). The control MIG vector that encodes an EGFP reporter gene was denoted as the Mock vector (See FIG. 1D and FIG. 1F).

Generation of Clonal HSPC-iNKT Cells Through Genetic Engineering of HSPCs miNKT-transduced bone marrow transfer in B6 mice was performed to generate the recipient mice denoted as B6-miNKT (See FIG. 2A). In brief, HSPC-enriched bone marrow cells harvested from donor B6 mice were cultured in vitro, transduced with either Mock or miNKT retroviral vectors, then separately transferred into irradiated recipient B6 mice. The recipient mice were allowed to reconstitute their immune system over the course of 6-8 weeks, followed by analysis to determine the presence of HSPC-iNKT cells. Desirable titers of the newly constructed miNKT retroviral vector, e.g., about 0.5-1×10⁶ infectious units (IFU)/mL (FIG. 5) were obtained and high efficiencies of HSPC transduction (routinely over about 50% of the cultured bone marrow cells) were achieved. Compared with the Mock-engineered recipient mice, denoted as B6-Mock, a significant increase of iNKT cells was observed in the B6-miNKT mice from thymus to peripheral tissues, suggesting the successful generation of HSPC-iNKT cells (See FIG. 2B and FIG. 2C). Through titrating the miNKT vector-transduced HSPCs used for bone marrow transfer, the increase of the iNKT cells from as high as 50% of the total αβ T cells, down to a desired level in the B6-miNKT mice was controlled (See FIG. 2D and FIG. 2E). The ability to regulate the number of HSPC-iNKT cells can be valuable for clinical applications of this HSPC-engineered iNKT cell strategy. Study of the HSPC-iNKT cells from the B6-miNKT mice revealed that these iNKT cells displayed a typical phenotype of mouse iNKT cells in that they exhibited high expression of the NK1.1 marker, as well as a memory T-cell signature (CD62L$^{lo}$CD44$^{hi}$) and a CD4⁺CD8⁻ or CD4⁻CD8⁻ co-receptor expression pattern (See FIG. 2F). Almost all of these HSPC-iNKT cells showed positive staining for TCR Vβ8, indicating that they expressed the transgenic clonal iNKT TCR and suggesting that they were derived from the miNKT-engineered HSPCs (See FIG. 2F). The production of high levels of HSPC-iNKT cells in the B6-miNKT mice persisted for up to 6 months following the initial bone marrow transfer and also post-secondary bone marrow transfer, highlighting the long-term effectiveness of this HSPC-engineered iNKT cell strategy (See FIG. 2G and FIG. 2H).

Functionality of HSPC-iNKT Cells

Then the functionality of the HSPC-iNKT cells was analyzed. When stimulated with α-GalCer in vitro, the HSPC-iNKT cells proliferated vigorously by over 20-fold in 5 days and produced large amounts of the effector cytokines IFN-γ and IL-4 (See FIGS. 2I-2K). When B6-miNKT mice were immunized with bone marrow-derived dendritic cells (BMDCs) loaded with α-GalCer, the HSPC-iNKT cells mounted a strong and rapid response in vivo, expanding close to 20-fold in 3 days (See FIG. 2L). Notably, the in vivo expansion of these cells peaked at day 3 post-immunization, compared with 7 days post-immunization for conventional αβ T cells. This speedy in vivo response is a signature of the HSPC-iNKT cells. These results indicate that the HSPC-iNKT cells are fully functional.

Development of HSPC-iNKT Cells

Next, the development of the HSPC-iNKT cells was analyzed. iNKT cell progenitors gated as TCRβ$^{lo}$mCD1d/PBS-57⁺ were detected in the thymus of the B6-miNKT mice and were found to follow a classic developmental path similar to that observed for endogenous iNKT progenitor cells in the control B6-Mock mice (See FIGS. 3A-3E). These progenitor cells appeared as CD4⁻CD8⁻ (DN), CD4⁺CD8⁺ (DP), and CD4⁺CD8⁻ (CD4 SP), corresponding with an iNKT development from DN to DP, then to CD4 SP or back to DN cells (See FIG. 3A). The expression of CD24, CD44, and DX5 markers on iNKT progenitor cells further defined their development in thymus into four stages: Stage 1 (CD24⁺CD44⁻DX5⁻), Stage 2 (CD24⁻CD44⁻DX5⁻), Stage 3 (CD24⁻CD44⁺DX5⁻), and Stage 4 (CD24⁻CD44⁺DX5⁺). Similar to their endogenous counterparts, TCR-transduced HSPC progenitors detected in the thymus of B6-miNKT mice followed a developmental path from Stages 1-4 (See FIG. 3B). In addition to their development in thymus to gain TCR expression (Control Point 1), iNKT cells also differ from conventional αβ T cells in that they need to undergo an additional maturation step in the periphery to acquire the expression of NK1.1 (Control Point 2). In B6-miNKT mice, HSPC-iNKT cells detected in the periphery did up-regulate NK1.1 expression compared with HSPC-iNKT cells detected in the thymus, similar to that observed for endogenous iNKT cells in the control B6-Mock mice (See FIG. 3C).

Overexpression of pre-rearranged aαβ TCR genes in HSPCs has been shown to induce allelic exclusion and block the rearrangements of endogenous TCR genes in the resulting conventional αβ T cells. Study of the HSPC-iNKT cells generated in the B6-miNKT mice revealed that these cells expressed the transgenic TCR (Vβ8⁺), but not the other TCR Vβ chains analyzed in the experiment (See FIG. 3D and FIG. 3E). In particular, these HSPC-iNKT cells did not express the TCR Vβ7 used by about 10% of endogenous iNKT cells (See FIG. 3D and FIG. 3E). Analysis of TCR α chain expression also showed an exclusion of other TCR Vα expression on the HSPC-iNKT cells (See FIG. 3D). These results suggest that the HSPC-iNKT cells give rise to clonal iNKT cells that express the transgenic iNKT TCRs, likely through an allelic exclusion mechanism during iNKT cell development in thymus.

The lineage differentiation of HSPC-iNKT cells was also studied. By detecting intracellular expression of transgenic iNKT TCRs (gated as Vβ8$^{intra+}$), TCR-transduced HSPCs and their progeny cells could be tracked (See FIG. 6A and FIG. 6B). Notably, because only T cells express the CD3 molecules that support the surface display of TCRs and their signaling, the other cells that lack CD3 molecules can only express the transgenic iNKT TCRs intracellularly, and these TCRs are not functional. In addition to generating iNKT cells, these results show that TCR-transduced HSPCs can also differentiate into all other blood cell lineages analyzed, including B cells (gated as CD19⁺), macrophages (gated as CD3⁻CD19⁻F4/80⁺), myeloid cells (gated as CD3⁻CD19⁻CD11b⁺), and granulocytes (gated as CD3⁻CD19⁻Gr-1⁺) (See FIG. 6A and FIG. 6B).

Antitumor Capacity of HSPC-iNKT Cells

The cancer therapy potential of the HSPC-iNKT cells was then studied. B6-miNKT mice and control B6-Mock mice were challenged with B16.F10 melanoma cells through i.v. injections and analyzed for lung metastasis 2 weeks later (See FIG. 4A). Experimental mice received immunization with either unloaded or α-GalCer-loaded BMDCs (denoted as BMDC/none or BMDC/α-GalCer, respectively) on Day 3 post tumor challenge to boost iNKT cell activities and to mimic a therapeutic vaccination treatment (See FIG. 4A). Monitoring of the HSPC-iNKT cells in the B6-miNKT mice showed that these cells actively responded to tumor challenge, evidenced by their expansion from about 1.5% to about 7% in blood (See FIG. 4B). In comparison, endogenous iNKT cells in the control B6-Mock mice also responded to tumor challenge, but their limiting starting number (<0.2%) only allowed them to reach about 1.7% in blood (See FIG. 4B). A significant protection from lung metastasis was observed in the B6-miNKT mice compared with that in the control B6-Mock mice, as evidenced by the reduction of both the number and size of tumor nodules (See FIGS. 4C-4E). Inclusion of a BMDC/α-GalCer immunization further expanded the HSPC-iNKT cells (up to about 30% in blood) (See FIG. 4B). However, no significant further reduction of lung tumor nodules was observed (See FIG. 4C), which may be due to a "saturation" of the antitumor capacity of iNKT cell-induced effector cells like NK cells and tumor-specific conventional au T cells that were limiting in mice. Total clearance of tumor metastasis likely requires combination therapy such as combining with adoptive transfer of additional effector cells. Notably, depigmentation of tumor nodules was observed in high numbers in the B6-iNKT mice (See FIG. 4F). Key molecules in the pigment synthesis pathway are a major class of tumor antigens for melanoma, and mutating or down-regulating these molecules are common strategies by which melanoma tumor cells escape immune attack, often leading to depigmentation. The presence of a large fraction of depigmented tumor nodules in the B6-miNKT mice therefore suggests a strong immune response against these tumors, presumably induced by the HSPC-iNKT cells through activation of antitumor NK and conventional αβ T cells (See FIG. 4F).

Human HSPC-iNKT Cells

Human HSPC-iNKT cells were successfully generated in BLT mice. Briefly, human iNKT TCR genes were cloned and inserted into an expression vector. Then human fetal liver CD34$^+$ HSPCs were transduced with the TCR expression vector and transplanted into NOD/SCID/IL-2rγ$^{-/-}$ mice that were pre-implanted with human fetal liver and thymus. Two to three months later, clonal human HSPC-iNKT cells were generated in the BLT mice. Thus, the present invention can be used to generate human HSPC-iNKT cells for cell therapies.

The following examples are intended to illustrate but not to limit the invention.

Materials and Methods

Mice and Materials

C57BL/6J (B6) mice were purchased from the Jackson Laboratory. Six- to ten-week-old females were used for all experiments unless otherwise indicated. All animal experiments were approved by the Institutional Animal Care and Use Committee of the University of California, Los Angeles.

α-Galactosylceramide (α-GalCer, KRN7000) was purchased from Avanti Polar Lipids; lipopolysaccharides (LPS) and 5-fluorouracil (5-FU) from Sigma; recombinant murine IL-3, IL-6 and stem cell factor (SCF) from PeproTech; and polybrene from Millipore. Fluorochrome-conjugated mCD1d/PBS-57 tetramer reagents were provided by the NIH Tetramer Core Facility (Emory University, Atlanta, Ga.). Fixable Viability Dye eFluor455UV was purchased from Affymetrix eBioscience.

Antibodies and Flow Cytometry

Fluorochrome-conjugated antibodies specific for mouse CD3, CD4, CD8, CD19, CD11b, CD24, CD62L, CD44, DX5, F4/80, Gr-1, TCRβ, TCR Vβ7, TCR Vβ8, and TCR Vα8.3 were purchased from BioLegend; for mouse NK1.1, IFN-γ, IL-4, TCR Vα2, TCR Vα3.2, TCR Vβ3, TCR Vβ4, TCR Vβ5, TCR Vβ6, TCR Vβ11, and TCR Vβ13, from BD Biosciences. Fc Block (anti-mouse CD16/32) was purchased from BD Biosciences. Cells were stained as previously described (Yang & Baltimore (2005) PNAS USA 102(12): 4518-4523) and analyzed using an LSRFortessa flow cytometer (BD Biosciences). FlowJo software was used to analyze the data.

ELISA

The ELISAs for detecting mouse cytokines were performed following a standard protocol from BD Biosciences. The capture and biotinylated antibody pairs for detecting mouse IFN-γ and IL-4 were also purchased from BD Biosciences. The streptavidin-HRP conjugate and mouse IFN-γ and IL-4 Single-Use ELISA Ready-Set-Go (RSG) Standards were purchased from Affymetrix eBioscience. The 3,3',5,5'-Tetramethylbenzidine (TMB) substrate was purchased from KPL. The samples were analyzed for absorbance at 450 nm using an Infinite M1000 microplate reader (Tecan).

Single-Cell iNKT TCR Cloning

The single-cell iNKT TCR RT-PCR was performed based on an established protocol (Smith, et al. (2009) Nat Protoc 4(3):372-384), with certain modifications. iNKT cells were sorted from mouse spleen cells based on a stringent forum of surface markers (CD3$^{lo}$mCD1d/PBS-57$^+$TCR Vβ8$^+$ NK1.1$^{hi}$) using a FACSAria II flow cytometer (BD Biosciences) (lo, low; hi, high). Single cells were sorted directly into PCR plates containing cell lysis buffer. The plates were then immediately flash frozen and stored at −80° C. until use. Upon thawing, the cell lysate from each cell was split in half on the same PCR plate and processed directly into iNKT TCR cloning for both α and β chain genes using a OneStep RTPCR kit (QIAGEN), following the manufacturer's instructions and using the iNKT TCR gene-specific primers. These primers were designed to amplify the ~200 bps spanning the CDR3 regions of the iNKT TCR α and β chain cDNAs and were customer-synthesized by Integrated DNA Technologies (IDT): for TCRα (forward primer: 5'-GGG AGA TAC TCA GCA ACT CTG GAT AAA GAT GC-3' (SEQ ID NO: 14); reverse primer: 5'-CCA GAT TCC ATG GTT TTC GGC ACA TTG-3' (SEQ ID NO: 15)) and for TCRβ (forward primer: 5'-GGA GAT ATC CCT GAT GGA TAC AAG GCC TCC-3' (SEQ ID NO: 16); reverse primer: 5'-GGG TAG CCT TTT GTT TGT TTG CAA TCT CTG-3' (SEQ ID NO: 17)). Verified sequences (productive germline Vα14-Jα18-Cα assembly for TCRα and Vβ8-D/J/N-Cβ assembly for TCRβ) were used to construct the complete cDNA sequences encoding the TCR α and β chains from a single cell, based on information about murine TCR genomic segments (the international ImMuno-GeneTics information system (IMGT), see WorldWideWebDOTimgtDOTorg, wherein "WorldWideWeb" is "www" and "DOT" is ".". The selected iNKT TCR α and β pair cDNAs were then synthesized as a single bicistonic gene, with codon optimization and a F2A sequence linking the TCRα and TCRβ cDNAs to enable their coexpression (GenScript).

The 293.T/mCD3 Stable Cell Line

HEK293.T human embryonic kidney epithelial cells (ATCC) were stably transduced with a lentiviral vector (Yang L, et al. (2008) Nat Biotechnol 26(3):326-334) coexpressing all four chains of mouse CD3 complex (CD3γ, CD3δ, CD3e, and CD3ζ), through linking the four cDNAs with three different 2A sequences (F2A, foot-and-mouth disease virus 2A; P2A, porcine teschovirus-1 2A; and T2A, Thosea asigna virus 2A). The transduced cells were then transiently transfected with an MOT1 vector encoding a mouse CD8 TCR, using a standard calcium precipitation procedure (Yang & Baltimore (2005) PNAS USA 102(12): 4518-4523). Single cells supporting the high surface expression of OT1 TCRs (gated as CD3$^+$TCR Vβ5$^+$) were sorted out using flow cytometry and grown into single-cell clones. A stable, single-cell clone, which lost OT1 TCR expression, but retained the capacity to support mouse TCR surface expression, was selected and designated as the 293.T/mCD3 stable cell line.

Mock and miNKT Retroviruses

Mock (MIG) retroviral vector was reported previously (Yang & Baltimore (2005) PNAS USA 102(12): 4518-4523). miNKT retroviral vector was constructed by inserting the synthetic bicistronic gene (iNKT TCRα-F2ATCRβ) into the MIG vector, replacing the IRES-EGFP segment. Retroviruses were made using HEK293.T cells, following a standard calcium precipitation protocol as previously described (Yang & Baltimore (2005) PNAS USA 102(12): 4518-4523).

HSPC Isolation, Transduction, Adoptive Transfer, and Secondary Bone Marrow Transfer The procedures were reported previously (Yang & Baltimore (2005) PNAS USA 102(12): 4518-4523). In brief, B6 mice were treated with 5-fluorouracil (250 μg per gram body weight). Five days later, bone marrow (BM) cells were harvested and cultured for 4 days in BM cell culture medium containing recombinant murine IL-3 (20 ng/mL), IL-6 (50 ng/mL), and SCF (50 ng/mL). On Days 2 and 3, BM cells were spin-infected with retroviruses supplemented with 8 μg/mL of polybrene, at 770×g, 30° C. for 90 minutes on Day 4, BM cells were collected and i.v. injected into B6 recipients that had received 1,200 rads of total body irradiation (about 1-2×10$^6$ transduced BM cells per recipient). For secondary BM transfer, fresh total BM cells harvested from the primary BM recipients were i.v. injected into secondary B6 recipient mice that had received 1,200 rads of total body irradiation (about 10×10$^6$ total BM cells per recipient). The BM recipient mice were maintained on the combined antibiotics sulfamethoxazole and trimethoprim oral suspension (Septra; Hi-Tech Pharmacal) in a sterile environment for 6-8 weeks until analysis or use for further experiments.

Bone Marrow-Derived Dendritic Cell Generation, Antigen Loading, and Mouse Immunization B6 mouse BMDCs were generated from BM cell cultures and matured with LPS as described previously (Yang & Baltimore (2005) PNAS USA 102(12): 4518-4523). The LPS-matured BMDCs were then cultured at 37° C. in a 6-well plate at 10×10$^6$ cells/well/2 mL BMDC culture medium containing 5 μg/mL of α-GalCer for 2 hours, with gentle shaking every 30 minutes. The α-GalCer-loaded BMDCs were then washed twice with PBS and used to immunize mice through i.v. injection (about 1×10$^6$ BMDCs/mouse).

In Vitro iNKT Cell Functional Assays

Spleen cells containing iNKT cells were cultured in vitro in a 24-well plate at 2×10$^6$ cells per well in regular mouse lymphocyte culture medium, with or without the addition of α-GalCer (100 ng/mL), for 5 days. On Days 3 and 5, cells were collected and assayed for iNKT cell expansion using flow cytometry, and the cell culture supernatants were collected and assayed for effector cytokine (IFN-γ and IL-4) production by ELISA. On Day 3, some cells were also treated with 4 μL/6 mL BD GolgiStop for 4-6 hours and then assayed for intracellular cytokine production using flow cytometry via intracellular staining using the BD Cytofix/Cytoperm Fixation/Permeabilization Kit (BD Biosciences).

In Vivo iNKT Cell Functional Assay

Mice were immunized with α-GalCer-loaded BMDCs through i.v. injection (about 1×10$^6$ BMDCs per mouse) and then periodically bled to monitor the in vivo iNKT cell responses using flow cytometry.

B16 Melanoma Lung Metastasis Mouse Model

Mice that received i.v. injection of 0.5-1×10$^6$ B16.F10 melanoma cells were allowed to develop lung metastasis over the course of 2 weeks (Fujii S, et al. (2002) Nat Immunol 3(9):867-874). On day 3 post tumor challenge, the experimental mice received i.v. injection of 1×10$^6$ BMDCs that were either unloaded or loaded with α-GalCer. On Day 14, mice were euthanized, and their lungs were harvested and analyzed for melanoma metastasis by counting tumor nodules under a Zeiss Stemi 2000-CS microscope (Carl Zeiss AG) at 10× magnification. Representative lungs were also analyzed by immunohistology.

Immunohistology

Lung tissues collected from the experimental mice were fixed in 10% neutral-buffered formalin and embedded in paraffin for sectioning (5 μm thickness), followed by hematoxylin and eosin staining using standard procedures (UCLA Translational Pathology Core Laboratory, Los Angeles, Calif.). The sections were imaged using an Olympus BX51 upright microscope equipped with an Optronics Macrofire CCD camera (AU Optronics) at 40× and 100× magnifications. The images were analyzed using Optronics Picture-Frame software (AU Optronics). Statistical analysis. Student's two-tailed t test was used for paired comparisons. Data are presented as mean±SEM, unless otherwise indicated. P<0.01 was considered significant.

Cloning of Human iNKT TCR Genes

Human iNKT TCR genes were cloned as above and with the following modifications. iNKT cells were sorted from fresh PBMCs of healthy human donors using flow cytometry based on a stringent forum of markers (gated as CD161$^+$CD3$^+$CD1d/α-GalCer$^+$Vα24-Jα18$^+$Vβ11$^+$). Single iNKT cells were sorted directly into PCR plates containing cell lysis buffer. The cell lysate from each single cells was then split into half on the same PCR plate, and be processed directly into iNKT TCR cloning for both α and β chains using a OneStep RT-PCR kit (Qiagen) following the manufacturer's instructions, and using the gene-specific primers verified by the preliminary study. The PCR products were then examined by electrophoresis and the amplicons corresponding to iNKT TCR α and β chains were sequenced. For each single cell, verification that it expressed an invariant alpha chain (Vα24-Jα18-Cα) and a semi-invariant beta chain (Vβ11-D/J/N-Cβ) helped to certify its iNKT identity, as well as reveal its unique TCRβ D/J/N sequence, with which a unique "iNKT TCR clone" was established. This cloning strategy exemplified in FIGS. 7A-7C was high-throughput, and a large collection of TCR clones from each iNKT subset were generated.

Construction of Human iNKT TCR Delivery Lentivectors

Human iNKT TCR genes were cloned into a chosen lentivector to generate lentiviral vectors that co-deliver the iNKT TCR genes as well as an EGFP reporter gene, denoted as phiNKT-EGFP (FIG. 8A). To facilitate the evaluation of lentivector-mediated TCR expression, the human embryonic kidney epithelial cell line 293.T was engineered to stably express all four chains of human CD3 (εγδζ), resulting in a 293.T/hCD3 cell line that allows for the surface display of human TCRs for their convenient detection (FIG. 8B). Transduction of the 293.T/hCD3 cells with the phiNKT-EGFP lentivectors revealed an efficient co-expression of the encoded human iNKT TCR genes and the EGFP report gene (FIG. 8C).

Generation of Human HSPC-iNKT Cells

Human fetal liver CD34$^+$ HSPCs were transduced with a selected phiNKT-EGFP lentivector. They were then transplanted into NOD/SCID/IL-2rγ$^{-/-}$ mice that were pre-implanted with human fetal liver and thymus, to generate iNKT TCR-engineered BLT mice (denoted as BLT-iNKT) following an established protocol. Two to three months later, the BLT mice were analyzed for the presence of human HSPC-iNKT cells (FIG. 9A). The data in FIG. 9B evidences that the methods of the present invention can be used to successfully generate clonal human HSPC-iNKT cells in iNKT TCR-engineered BLT mice.

iNKT TCR Sequences

Because invariant natural killer T (iNKT) cells express T cell receptors (TCRs) comprising the identical alpha chains and beta chains of limited diversity, the full sequence of one alpha chain is listed as being exemplary, however, other alpha chains can be implemented according to the present invention. Similarly, for the beta chains, the full sequence of one beta chain and the sequences of the diverse region (D/J/N region) of a variety of beta chains are listed for exemplary purposes, but other beta chains can be implemented according to the present invention. As an example, beta chains that utilize the human TCR V beta 11 segment were used. Therefore, the TCR beta V regions of these beta chains are identical, leaving the D/J/N segment the only diverse regions in these iNKT TCR beta chains. The genomic sequence, codon-optimized gene sequence and protein sequence of each iNKT TCR alpha and beta chains are listed below. Each unique D/J/N region makes a unique beta chain, which in combination with the identical alpha chain forms a unique iNKT TCR pair.

Human iNKT TCR Alpha Chain Full Sequence
(Identical for All Human iNKT TCRs) cDNA Genomic
Sequence (831 bp)
(SEQ ID NO: 18)
atgaaaaagcatctgacgaccttcttggtgattttgtggctttattt tataggggaatggcaaaaaccaagtggagcagagtcctcagtccctg atcatcctggagggaaagaactgcactcttcaatgcaattatacagtg agccccttcagcaacttaaggtggtataagcaagatactgggagaggt cctgtttccctgacaatcatgactttcagtgagaacacaaagtcgaac ggaagatatacagcaactctggatgcagacacaaagcaaagctctctg cacatcacagcctcccagctcagcgattcagcctcctacatctgtgtg gtgagcgacagaggctcaaccctggggaggctatactttggaagagga actcagttgactgtctggcctgatatccagaaccctgaccctgccgtg taccagctgagagactctaaatccagtgacaagtctgtctgcctattc accgattttgattctcaaacaaatgtgtcacaaagtaaggattctgat gtgtatatcacagacaaaactgtgctagacatgaggtctatggacttc aagagcaacagtgctgtggcctggagcaacaaatctgactttgcatgt gcaaacgccttcaacaacagcattattccagaagacaccttcttcccc agcccagaaagttcctgtgatgtcaagctggtcgagaaaagctttgaa acagatacgaacctaaactttcaaaacctgtcagtgattgggttccga atcctcctcctgaaagtggccgggttaatctgctcatgacgctgcgg ctgtggtccagctga
cDNA Codon-Optimized Sequence (831 bp)
(SEQ ID NO: 19)
atgaaaaagcatctgacaacattcctggtcattctgtggctgtacttc taccgaggcaacggcaaaaatcaggtggagcagtccccacagtccctg atcattctggagggaagaactgcactctgcagtgtaattacaccgtg tctccctttagtaacctgcgctggtataaacaggacaccggacgagga cccgtgagcctgacaatcatgactttctcagagaacacaaagagcaat ggacggtacaccgctacactggacgcagataccaaacagagctcccctg cacatcacagcatctcagctgtcagatagcgcctcctacatttgcgtg gtctctgaccgagggagtaccctgggccgactgtattttggaaggggg acccagctgacagtgtggcccgacatccagaaccccagatccgccgtc taccagctcgcgagacagcaagtctagtgataaaagcgtgtgcctgttc acagactttgattctcagactaatgtctctcagagtaaggacagtgac gtgtacattactgacaaaaccgtcctggatatgaggagcatggacttc aagtcaaacagcgccgtggcttggtcaaacaagagcgacttcgcatgc gccaatgatttaacaattcaatcattccagaggataccttattcctag cccagaatcaagctgtgacgtgaagctggtcgagaaaagtttcgaaac tgataccaacctgaattttcagaacctgtctgtgatcggcttcagaat cctgctgctgaaggtcgccggctttaatctgctgatgacactgagact gtggtcctcttga
Protein Sequence (276 aa)
(SEQ ID NO: 20)
MKKHLTTFLVILWLYFYRGNGKNQVEQSPQSLIILEGKNCTLQCNYTV

SPFSNLRWYKQDTGRGPVSLTIMTFSENTKSNGRYTATLDADTKQSSL

HITASQLSDSASYICVVSDRGSTLGRLYFGRGTQLTVWPDIQNPDPAV

YQLRDSKSSDKSVCLFTDFDSQTNVSQSKDSDVYITDKTVLDMRSMDF

KSNSAVAWSNKSDFACANAFNNSIIPEDTFFPSPESSCDVKLVEKSFE

TDTNLNFQNLSVIGFRILLLLKVAGFNLLMTLRLWSS

Human iNKT TCR Beta Chain Full Sequence (the
D/J/N regions are in bold) cDNA Genomic Sequence
(870 bp + D/J/N)
atgactatcaggctcctctgctacatgggcttttattttctgggggca ggcctcatggaagctgacatctaccagaccccaagataccttgttata gggacaggaagaagatcactctggaatgttctcaaaccatgggccat gacaaaatgtactggtatcaacaagatccaggaatggaactacacctc atccactattcctatggagttaattccacagagaagggagatctttcc tctgagtcaacagtctccagaataaggacggagcattttcccctgacc ctggagtctgccaggccctcacatacctctcagtacctctgtgccagc

(D/J/N) gaggacctgaacaaggtgttcccaccccgaggtcgctgtgtt tgagccatcagaagcagagatctcccacacccaaaaggccacactggt gtgcctggccacaggcttcttccctgaccacgtggagctgagctggtg ggtgaatgggaaggaggtgcacagtggggtcagcacggaccccgcagcc cctcaaggagcagcccgccctcaatgactccagatactgcctgagcag ccgcctgagggtctcggccaccttctggcagaaccccgcaaccactt ccgctgccaagtccagttctacgggctctcggagaatgacgagtggac ccaggatagggccaaacccgtcacccagatcgtcagcgccgaggcctg gggtagagcagactgtggcttacctcggtgtcctaccagcaagggt cctgtctgccaccatcctctatgagatcctgctaggaaggccaccct gtatgctgtgctggtcagcgcccttgtgttgatggccatggtcaagag aaaggatttctga (SEQ ID NO: 21 is the sequence before
the D/J/N region and SEQ ID NO: 63 is the sequence
after the D/N/J region)

cDNA Codon-Optimized Sequence (870 bp + D/J/N)
atgaccatccggctgctgtgctacatgggcttctattttctgggggca ggcctgatggaagccgacatctaccagactcccagatacctggtcatc ggaaccgggaagaaaattacactggagtgttcccagacaatgggccac gataagatgtactggtatcagcaggaccctgggatgaactgcacctg -continued atccattactcctatggcgtgaactctaccgagaagggcgacctgagc agcgaatccaccgtctctcgaattaggacagagcactttcctctgact ctggaaagcgcccgaccaagtcatacatcacagtacctgtgcgctagc

(D/J/N)gaggacctgaataaggtgttccccctgaggtggctgtctt tgaaccaagtgaggcagaaatttcacatacacagaaagccaccctggt gtgcctggctaccggcttcttcccgatcacgtggagctgagctggtg ggtcaacggcaaggaagtgcatagcggagtctccacagacccacagcc cctgaaagagcagcctgctctgaatgattccagatactgctgtctag tagactgcgggtgtctgccaccttctggcagaacccaaggaatcattt cagatgtcaggtgcagttttatggcctgagcgagaacgatgaatggac tcaggacagggctaagccagtgacccagatcgtcagcgcagaggcctg gggaagagcagactgcgggtttacaagcgtgagctatcagcagggcgt cctgagcgccacaatcctgtacgaaattctgctgggaaaggccactct gtatgctgtgctggtctccgctctggtgctgatggcaatggtcaagcg gaaagatttctga (SEQ ID NO: 22 is the sequence before the D/J/N region and SEQ ID NO: 64 is the sequence after the D/N/J region)

Protein Sequence (289 aa + D/J/N)
MTIRLLCYMGFYFLGAGLMEADIYQTPRYLVIGTGKKITLECSQTMGH

DKMYWYQQDPGMELHLIHYSYGVNSTEKGDLSSESTVSRIRTEHFPLT

LESARPSHTSQYLCAS(D/J/N)EDLNKVFPPEVAVFEPSEAEISHTQ

KATLVCLATGFFPDHVELSWWVNGKEVHSGVSTDPQPLKEQPALNDSR

YCLSSRLRVSATFWQNPRNHFRCQVQFYGLSENDEWTQDRAKPVTQIV

SAEAWGRADCGFTSVSYQQGVLSATILYEILLGKATLYAVLVSALVLM

AMVKRKDF (SEQ ID NO: 23 is the sequence before the D/J/N region and SEQ ID NO: 65 is the sequence after the D/N/J region)

Human iNKT TCR Beta Chain Diverse Region (D/J/N) Sequence
Human iNKT TCR Beta Chain Cloned from the CD4+ CD8- (CD4 SP) Subpopulation cDNA Genomic Sequence (60 bp)
(SEQ ID NO: 24)
GTAGCGGTTGGGCCCCAAGAGACCCAGTACTTCGGGCCAGGCACGCGG

CTCCTGGTGCTC cDNA Codon-Optimized Sequence (60 bp)
(SEQ ID NO: 25)
GTGGCAGTCGGACCTCAGGAGACCCAGTACTTCGGACCCGGCACCCGC

CTGCTGGTGCTG

Protein Sequence (20 aa)
(SEQ ID NO: 26)
VAVGPQETQYFGPGTRLLVL

Human iNKT TCR Beta Chain Cloned from the CD4+ CD8- (CD4 SP) Subpopulation cDNA Genomic Sequence (54 bp)
(SEQ ID NO: 27)
AGTGGGCCAGGGTACGAGCAGTACTTCGGGCCGGGCACCAGGCTCACG

GTCACA cDNA Codon-Optimized Sequence (54 bp)
(SEQ ID NO: 28)
TCAGGACCCGGCTACGAGCAGTATTTCGGCCCCGGAACTCGGCTGACC

GTGACC

Protein Sequence (18 aa)
(SEQ ID NO: 29)
SGPGYEQYFGPGTRLTVT

Human iNKT TCR Beta Chain Cloned from the CD4+ CD8- (CD4 SP) Subpopulation cDNA Genomic Sequence (57 bp)
(SEQ ID NO: 30)
AGTCCCCAATTAAACACTGAAGCTTTCTTTGGACAAGGCACCAGACTC

ACAGTTGTA cDNA Codon-Optimized Sequence (57 bp)
(SEQ ID NO: 31)
TCTCCACAGCTGAACACCGAGGCCTTCTTCGGGCAGGGCACAAGGCTT

ACCGTGGTG

Protein Sequence (19 aa)
(SEQ ID NO: 32)
SPQLNTEAFFGQGTRLTVV

Human iNKT TCR Beta Chain Cloned from the CD4+ CD8- (CD4 SP) Subpopulation cDNA Genomic Sequence (78 bp)
(SEQ ID NO: 33)
AGTGAATTGCGGGCGCTCGGGCCCAGCTCCTATAATTCACCCCTCCAC

TTTGGGAACGGGACCAGGCTCACTGTGACA cDNA Codon-Optimized Sequence (78 bp)
(SEQ ID NO: 34)
TCCGAACTCCGAGCCCTGGGGCCTAGCTCCTACAATAGCCCCCTGCAC

TTTGGCAACGGAACCAGGCTGACGGTCACC

Protein Sequence (26 aa)
(SEQ ID NO: 35)
SELRALGPSSYNSPLHFGNGTRLTVT

Human iNKT TCR Beta Chain Cloned from the CD4+ CD8- (CD4 SP) Subpopulation cDNA Genomic Sequence (60 bp)
(SEQ ID NO: 36)
AGTGAACAGGGGACTACTGCGGGAGCTTTCTTTGGACAAGGCACCAGA

CTCACAGTTGTA cDNA Codon-Optimized Sequence (60 bp)
(SEQ ID NO: 37)
TCCGAACAGGGAACCACAGCAGGAGCCTTCTTCGGTCAGGGAACAAGA

CTGACAGTCGTG

Protein Sequence (20 aa)
(SEQ ID NO: 38)
SEQGTTAGAFFGQGTRLTVV

Human iNKT TCR Beta Chain Cloned from the CD4- CD8+ (CD8 SP) Subpopulation cDNA Genomic Sequence (66 bp)
(SEQ ID NO: 39)
AGTGAGTCACGACATGCGACAGGAAACACCATATATTTTGGAGAGGGA

AGTTGGCTCACTGTTGTA cDNA Codon-Optimized Sequence (66 bp)
(SEQ ID NO: 40)
AGCGAGAGCAGGCACGCAACCGGGAACACCATATACTTTGGCGAGGGC

TCCTGGCTGACTGTGGTG

-continued

Protein Sequence (22 aa)
(SEQ ID NO: 41)
SESRHATGNTIYFGEGSWLTVV

Human iNKT TCR Beta Chain Cloned from the CD4-
CD8+ (CD8 SP) Subpopulation cDNA Genomic
Sequence (69 bp)
(SEQ ID NO: 42)
AGTGTACCCGGGAACGACAGGGGCAATGAAAAACTGTTTTTGGCAGT

GGAACCCAGCTCTCTGTCTTG cDNA Codon-Optimized Sequence (69 bp)
(SEQ ID NO: 43)
TCCGTGCCTGGCAACGATAGAGGTAACGAGAAGCTGTTTTTCGGATCC

GGCACACAGCTGTCTGTCCTG

Protein Sequence (23 aa)
(SEQ ID NO: 44)
SVPGNDRGNEKLFFGSGTQLSVL

Human iNKT TCR Beta Chain Cloned from the CD4-
CD8+ (CD8 SP) Subpopulation cDNA Genomic
Sequence (72 bp)
(SEQ ID NO: 45)
AGTGAAGGGGGGGGCCTTAAGCTAGCCAAAAACATTCAGTACTTCGGC

GCCGGGACCCGGCTCTCAGTGCTG cDNA Codon-Optimized Sequence (72 bp)
(SEQ ID NO: 46)
AGTGAGGGAGGGGGACTGAAGCTGGCTAAGAATATTCAGTACTTCGGC

GCCGGCACTAGACTGTCTGTGCTG

Protein Sequence (24 aa)
(SEQ ID NO: 47)
SEGGGLKLAKNIQYFGAGTRLSVL

Human iNKT TCR Beta Chain Cloned from the CD4-
CD8- (DN) Subpopulation cDNA Genomic
Sequence (69 bp)
(SEQ ID NO: 48)
AGTGAATTCGCCTCTTCGGTACGTGGAAACACCATATATTTTGGAGAG

GGAAGTTGGCTCACTGTTGTA cDNA Codon-Optimized Sequence (69 bp)
(SEQ ID NO: 49)
TCTGAGTTCGCGAGCAGCGTCCGGGGTAATACCATTTACTTCGGGGAA

GGCAGCTGGCTGACCGTGGTG

Protein Sequence (23 aa)
(SEQ ID NO: 50)
SEFASSVRGNTIYFGEGSWLTVV

Human iNKT TCR Beta Chain Cloned from the CD4-
CD8- (DN) Subpopulation cDNA Genomic
Sequence (60 bp)
(SEQ ID NO: 51)
AGTGCGGCATTAGGCCGGGAGACCCAGTACTTCGGGCCAGGCACGCGG

CTCCTGGTGCTC cDNA Codon-Optimized Sequence (60 bp)
(SEQ ID NO: 52)
TCTGCAGCCCTTGGCCGAGAGACTCAGTACTTCGGCCCTGGCACAAGA

CTGCTCGTGCTC

Protein Sequence (20 aa)
(SEQ ID NO: 53)
SAALGRETQYFGPGTRLLVL

Human iNKT TCR Beta Chain Cloned from the CD4-
CD8- (DN) Subpopulation cDNA Genomic
Sequence (63 bp)
(SEQ ID NO: 54)
AGTGCCTCCGGGGGTGAATCCTACGAGCAGTACTTCGGGCCGGGCACC

AGGCTCACGGTCACA cDNA Codon-Optimized Sequence (63 bp)
(SEQ ID NO: 55)
AGCGCCTCCGGAGGAGAGTCATACGAACAGTATTTCGGCCCTGGCACA

CGCCTCACTGTGACC

Protein Sequence (21 aa)
(SEQ ID NO: 56)
SASGGESYEQYFGPGTRLTVT

Human iNKT TCR Beta Chain Cloned from the CD4-
CD8- (DN) Subpopulation cDNA Genomic
Sequence (90 bp)
(SEQ ID NO: 57)
AGCGGTCGGGTCTCGGGGGGCGATTCCCTCATAGCGTTTCTAGGCCAA

GAGACCCAGTACTTCGGGCCAGGCACGCGGCTCCTGGTGCTC cDNA Codon-Optimized Sequence (90 bp)
(SEQ ID NO: 58)
TCAGGACGAGTGTCCGGAGGGGATAGCCTCATCGCATTTCTGGGGCAG

GAAACTCAGTACTTCGGACCCGGAACACGCCTCCTGGTGCTG

Protein Sequence (30 aa)
(SEQ ID NO: 59)
SGRVSGGDSLIAFLGQETQYFGPGTRLLVL

Human iNKT TCR Beta Chain Cloned from the CD4-
CD8- (DN) Subpopulation cDNA Genomic
Sequence (69 bp)
(SEQ ID NO: 60)
AGTGTACCCGGGAACGACAGGGGCAATGAAAAACTGTTTTTGGCAGT

GGAACCCAGCTCTCTGTCTTG cDNA Codon-Optimized Sequence (69 bp)
(SEQ ID NO: 61)
TCCGTGCCTGGCAACGATAGAGGTAACGAGAAGCTGTTTTTCGGATCC

GGCACACAGCTGTCTGTCCTG

Protein Sequence (23 aa)
(SEQ ID NO: 62)
SVPGNDRGNEKLFFGSGTQLSVL

Statistical Analysis

Student's two-tailed t test was used for paired comparisons. Data are presented as mean±SEM, unless otherwise indicated. P<0.01 was considered significant.

To the extent necessary, the following are herein incorporated by reference:

Restifo, N. P., Dudley, M. E. & Rosenberg, S. A. Adoptive immunotherapy for cancer: harnessing the T cell response. Nat Rev Immunol 12, 269-281, doi:10.1038/nri3191 (2012).

Vivier, E., Ugolini, S., Blaise, D., Chabannon, C. & Brossay, L. Targeting natural killer cells and natural killer T cells in cancer. Nat Rev Immunol 12, 239-252, doi:10.1038/nri3174 (2012).

Berzins, S. P., Smyth, M. J. & Baxter, A. G. Presumed guilty: natural killer T cell defects and human disease. Nat Rev Immunol 11, 131-142, doi:10.1038/nri2904 (2011).

Bendelac, A., Savage, P. B. & Teyton, L. The biology of NKT cells. Annu Rev Immunol 25, 297-336, doi:10.1146/annurev.immunol.25.022106.141711 (2007).

Yang, L. & Baltimore, D. Long-term in vivo provision of antigen-specific T cell immunity by programming hematopoietic stem cells. PNAS USA 102, 4518-4523, doi: 10.1073/pnas.0500600102 (2005).

Giannoni, F. et al. Allelic exclusion and peripheral reconstitution by TCR transgenic T cells arising from transduced human hematopoietic stem/progenitor cells. Molecular therapy: the journal of the American Society of Gene Therapy 21, 1044-1054, doi:10.1038/mt.2013.8 (2013).

Vatakis, D. N. et al. Antitumor activity from antigen-specific CD8 T cells generated in vivo from genetically engineered human hematopoietic stem cells. PNAS USA 108, E1408-1416, doi:10.1073/pnas.1115050108 (2011).

Fujii, S., Shimizu, K., Kronenberg, M. & Steinman, R. M. Prolonged IFN-gamma-producing NKT response induced with alpha-galactosylceramide-loaded DCs. Nat Immunol 3, 867-874, doi: 10.1038/ni827 (2002).

Lockridge, J. L. et al. Analysis of the CD1 antigen presenting system in humanized SCID mice. PLoS One 6, e21701, doi:10.1371/journal.pone.0021701 (2011).

Sondergaard, J. N. et al. Differential sensitivity of melanoma cell lines with BRAFV600E mutation to the specific Raf inhibitor PLX4032. J Transl Med 8, 39, doi:10.1186/1479-5876-8-39 (2010).

Godfrey, D. I. & Berzins, S. P. Control points in NKT-cell development. Nat Rev Immunol 7, 505-518, doi:10.1038/nri2116 (2007).

Watarai, H., Nakagawa, R., Omori-Miyake, M., Dashtsoodol, N. & Taniguchi, M. Methods for detection, isolation and culture of mouse and human invariant NKT cells. Nat Protoc 3, 70-78, doi:10.1038/nprot.2007.515 (2008).

Mattarollo, S. R. et al. NKT cell adjuvant-based tumor vaccine for treatment of myc oncogene-driven mouse B-cell lymphoma. Blood 120, 3019-3029, doi: 10.1182/blood-2012-04-426643 (2012).

Sznol, M. & Chen, L. Antagonist antibodies to PD-1 and B7-H1 (PD-L1) in the treatment of advanced human cancer. Clinical cancer research: an official journal of the American Association for Cancer Research 19, 1021-1034, doi: 10.1158/1078-0432.CCR-12-2063 (2013).

Morrison, S. J., Uchida, N. & Weissman, I. L. The biology of hematopoietic stem cells. Annu Rev Cell Dev Biol 11, 35-71, doi:10.1146/annurev.cb.11.110195.000343 (1995).

Baltimore, D., Witte, O. N., Yang, L., Economou, J. & Ribas, A. Overcoming barriers to programming a therapeutic cellular immune response to fight melanoma. Pigment Cell Melanoma Res 23, 288-289, doi:10.1111/j.1755-148X.2010.00666.x (2010).

Chodon, T. et al. Adoptive transfer of MART-1 T-cell receptor transgenic lymphocytes and dendritic cell vaccination in patients with metastatic melanoma. Clinical cancer research: an official journal of the American Association for Cancer Research 20, 2457-2465, doi:10.1158/1078-0432.CCR-13-3017 (2014).

O'Connell, R. M. et al. Lentiviral vector delivery of human interleukin-7 (hIL-7) to human immune system (HIS) mice expands T lymphocyte populations. PLoS One 5, e12009, doi:10.1371/journal.pone.0012009 (2010).

Chung B. A. H, G. S., Blumberg G., Klein S., Zhu J., Parekh C., Arumugam B., Yang O., Crooks G. M. Engineering the human thymic microenvironment to manipulate thymopoiesis in vivo. Stem Cells 32(9):2386-2396 (2014).

Blumenthal, M. et al. Effective suicide gene therapy for leukemia in a model of insertional oncogenesis in mice. Molecular therapy: the journal of the American Society of Gene Therapy 15, 183-192, doi:10.1038/sj.mt.6300015 (2007).

Bendelac, A., Savage, P. B. & Teyton, L. The biology of NKT cells. Annu Rev Immunol 25, 297-336 (2007).

Luo, X. M. et al. Engineering human hematopoietic stem/progenitor cells to produce a broadly neutralizing anti-HIV antibody after in vitro maturation to human B lymphocytes. Blood 113, 1422-31 (2009).

Hur, E. M. et al. Inhibitory effect of HIV-specific neutralizing IgA on mucosal transmission of HIV in humanized mice. Blood 120, 4571-82 (2012).

Sun et al. Invariant natural killer T cells generated from human adult hematopoietic stem-progenitor cells are poly-functional. Cytokine 72:48-57 (2015).

Tian et al. The development of genetically modified K562 cells as artificial antigen presenting cells for NKT cells J. Immunol., 190: 45.3 (2013).

All scientific and technical terms used in this application have meanings commonly used in the art unless otherwise specified.

As used herein, the term "subject" includes humans and non-human animals. The term "non-human animal" includes all vertebrates, e.g., mammals and non-mammals, such as non-human primates, horses, sheep, dogs, cows, pigs, chickens, and other veterinary subjects and test animals.

The use of the singular can include the plural unless specifically stated otherwise. As used in the specification and the appended claims, the singular forms "a", "an", and "the" can include plural referents unless the context clearly dictates otherwise. The use of "or" can mean "and/or" unless stated otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of making an engineered functional iNKT cell genetically modified to contain at least one exogenous invariant natural killer T cell receptor (iNKT TCR) nucleic acid molecule, the method comprising transducing a human hematopoietic stem or progenitor cell (HSPC) with the at least one exogenous invariant natural killer T cell receptor (iNKT TCR) nucleic acid molecule so that the human hematopoietic stem or progenitor cell transduced by the exogenous iNKT TCR nucleic acid molecule expresses an iNKT TCR comprising an invariant alpha chain polypeptide and a semi-invariant beta chain polypeptide.

2. The method of claim 1, which further comprises expanding the cell transduced with the iNKT TCR nucleic acid molecule in vitro.

3. The method of claim 1, which further comprises engrafting the cell transduced with the iNKT TCR nucleic acid molecule in a subject to generate clonal populations of the engineered cell.

4. The method of claim 3, wherein the subject contains human thymus tissue.

5. The method of claim 1, which further comprises cloning the T cell receptor of the invariant natural killer T cell.

6. The method of claim 1, wherein the iNKT TCR nucleic acid molecule is contained in an expression vector.

7. The method of claim 1, wherein the iNKT TCR nucleic acid molecule encodes for one or more polypeptides comprising an invariant alpha chain polypeptide and a semi-invariant beta chain polypeptide from a human iNKT T cell receptor.

8. The method of claim 1, wherein the engineered iNKT cell lacks exogenous oncogenes.

9. The method of claim 1, wherein the iNKT TCR nucleic acid molecule encodes a T cell receptor that recognizes a-galactosylceramide (a-GalCer).

10. The method of claim 1, wherein the engineered cell is capable of producing one or more cytokines and/or chemokines selected from IFNγ, TNFα, TGFβ, GM-CSF, IL-2, IL-4, IL-5, IL-6, IL-10, IL-13, IL-17, IL-21, RANTES, Eotaxin, MIP-1α, and MIP-1β.

11. The method of claim 1, wherein the method further comprises expanding the engineered iNKT cell to make a clonal population of engineered iNKT cells.

12. The method of claim 11, wherein the cell is co-cultured with OP9-DL1 or MS5-DL4 stromal cells.

13. The method of claim 11, wherein the method further comprises contacting the transduced cell with an agonist antigen, wherein the iNKT TCR nucleic acid molecule encodes a T cell receptor that recognizes a-galactosylceramide (a-GalCer), and wherein the agonist antigen comprises a-GalCer.

14. The method of claim 13, wherein the method further comprises co-culturing the cells with peripheral blood mononuclear cells, antigen presenting cells, or artificial antigen presenting cells.

15. The method of claim 1, wherein the engineered cell comprises suppression of endogenous TCRs.

16. A cell produced by the method of claim 1.

17. A method of treating a subject in need of invariant natural killer T cells, which comprises administering to the subject the cell of claim 16.

18. The method of claim 1, wherein the cell is a CD34+ HSPC.

19. The method of claim 18, wherein the CD34+ HSPC is isolated from cord blood or peripheral blood.

* * * * *